US006514741B1

(12) United States Patent
Presnell et al.

(10) Patent No.: US 6,514,741 B1
(45) Date of Patent: Feb. 4, 2003

(54) TRYPTASE-LIKE POLYPEPTIDE ZTRYP1

(75) Inventors: Scott R. Presnell, Tacoma, WA (US); David W. Taft, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/636,382

(22) Filed: Aug. 9, 2000

Related U.S. Application Data

(60) Provisional application No. 60/149,563, filed on Aug. 18, 1999.

(51) Int. Cl.[7] ............................ C12N 9/48; C07K 14/00
(52) U.S. Cl. ......................... 435/212; 530/300; 530/350
(58) Field of Search ................................ 530/300, 350; 435/212

(56) References Cited

FOREIGN PATENT DOCUMENTS

EP 0 419 2952 3/1991

OTHER PUBLICATIONS

Vanderslice, P. et al., *Proc. Nat'l. Acad. Sci. USA 87*:3811–3815, 1990.
Wenzel, S. Et al., J. Immunol. *Methods 86*:139–142, 1986.
Enander, I. Et al., J. Immunol. *Methods 138*:39–46, 1991.
Lexicon Genetics, Inc. Omnibank OST, 1998: OST19165.
Lexicon Genetics, Inc. Omnibank OST, 1998: OST17115.
Lexicon Genetics, Inc. Omnibank OST, 1998: OST3158.
Lexicon Genetics, Inc. Omnibank OST, 1998: OST17131.
Lexicon Genetics, Inc. Omnibank OST, 1998: OST18563.
Lexicon Genetics, Inc. Omnibank OST, 1998: OST1193.
Lexicon Genetics, Inc. Omnibank OST, 1998: OST2863.
Lexicon Genetics, Inc. Omnibank OST, 1998: OST2623.
Lexicon Genetics, Inc. Omnibank OST, 1998: OST11243.
Lexicon Genetics, Inc. Omnibank OST, 1998: OST27606.
Lexicon Genetics, Inc. Omnibank OST, 1998: OST21726.
Lexicon Genetics, Inc. Omnibank OST, 1998: OST61591.
Strausberg, R. National Cancer Institute, Cancer Genome Anatomy Project, 1997; Genbank Accession No: AW183721.

*Primary Examiner*—Remy Yucel
*Assistant Examiner*—Bronwen M. Loeb
(74) *Attorney, Agent, or Firm*—Jennifer K. Johnson

(57) ABSTRACT

The present invention relates to polynucleotide and polypeptide molecules for mouse ztryp1, a novel member of the serine protease family of proteins. The polynucleotides encoding mouse ztryp1 can be used to identify a human ortholog or to create a mouse model associated with human disease states. The present invention also includes methods for producing the protein, uses therefor and antibodies thereto.

5 Claims, No Drawings

SEQUENCE LISTING

```
<160> NUMBER OF SEQ ID NOS: 24

<210> SEQ ID NO 1
<211> LENGTH: 1154
<212> TYPE: DNA
<213> ORGANISM: Mus musculus
<220> FEATURE:
<221> NAME/KEY: CDS
<222> LOCATION: (29)...(970)

<400> SEQUENCE: 1

aggagcagta agggctggac tctgtgcc atg gcg tgt gga tca gtg gat cct        52
                                Met Ala Cys Gly Ser Val Asp Pro
                                 1               5

cac ggt ctt ctc tcc tct cca ctt gct tct gcc aga ctt aat agt ctg      100
His Gly Leu Leu Ser Ser Pro Leu Ala Ser Ala Arg Leu Asn Ser Leu
     10                  15                  20

ccc tat atg gaa ggt ccc tgg atc tgg tcc tgt ggt cag acc aac ata      148
Pro Tyr Met Glu Gly Pro Trp Ile Trp Ser Cys Gly Gln Thr Asn Ile
 25                  30                  35                  40

acc tgc aag gtg gta aat ggg aag gcg gtg gaa gta ggc aag tgg ccg      196
Thr Cys Lys Val Val Asn Gly Lys Ala Val Glu Val Gly Lys Trp Pro
                 45                  50                  55

tgg cag gta agc att ctt ttc ctg gga atg tac atc tgc agc ggc tcc      244
Trp Gln Val Ser Ile Leu Phe Leu Gly Met Tyr Ile Cys Ser Gly Ser
             60                  65                  70

ctc atc cac cac cac tgg atc ctc acc gct gca cac tgc tta caa aga      292
Leu Ile His His His Trp Ile Leu Thr Ala Ala His Cys Leu Gln Arg
         75                  80                  85

tcc aag aac ccg gct aaa tac act gtg aag gtg gga gtc cag acc ctc      340
Ser Lys Asn Pro Ala Lys Tyr Thr Val Lys Val Gly Val Gln Thr Leu
     90                  95                  100

cca gac aac agc acc tct gag ctc ctg gtc act aga att gta att cac      388
Pro Asp Asn Ser Thr Ser Glu Leu Leu Val Thr Arg Ile Val Ile His
105                 110                 115                 120

gag aac ttc atc aat cgc atg tct gac gac atc gcc atc ctg aag ctc      436
Glu Asn Phe Ile Asn Arg Met Ser Asp Asp Ile Ala Ile Leu Lys Leu
                125                 130                 135

aag tat cct gtc act tgg tcc ccc ctc gtc cag cca atc tgt ctc ccc      484
Lys Tyr Pro Val Thr Trp Ser Pro Leu Val Gln Pro Ile Cys Leu Pro
            140                 145                 150

tca ttc aat tta aag cca agc att gga acc atg tgc tgg gtc gtc ggg      532
Ser Phe Asn Leu Lys Pro Ser Ile Gly Thr Met Cys Trp Val Val Gly
        155                 160                 165
```

-continued

```
tgg gga ctt gaa aag gcc gaa ggg cac cca aag act ccc tat agt gtc      580
Trp Gly Leu Glu Lys Ala Glu Gly His Pro Lys Thr Pro Tyr Ser Val
    170                 175                 180

caa ggt ttg gct gtc agg att gtg aac aat gaa atc tgc aat cat cgg      628
Gln Gly Leu Ala Val Arg Ile Val Asn Asn Glu Ile Cys Asn His Arg
185                 190                 195                 200

tac cag ttc ctc ctg ctg aag aac cag aaa aag ttc att ggg aac gac      676
Tyr Gln Phe Leu Leu Leu Lys Asn Gln Lys Lys Phe Ile Gly Asn Asp
                205                 210                 215

atg ttg tgt aca agc tca gaa tgg ggc ctg gac act tgt cag gac acc      724
Met Leu Cys Thr Ser Ser Glu Trp Gly Leu Asp Thr Cys Gln Asp Thr
            220                 225                 230

tcc gga agc tct ctg gtt tgc cag atg aac aag acc tgg gtc cag atg      772
Ser Gly Ser Ser Leu Val Cys Gln Met Asn Lys Thr Trp Val Gln Met
        235                 240                 245

ggc gtg gtg agc tgg aac ttt gac tgt ggc cgt cgc caa ttc cca agc      820
Gly Val Val Ser Trp Asn Phe Asp Cys Gly Arg Arg Gln Phe Pro Ser
    250                 255                 260

gtc tac acc agc acc tcc cac ttc acc cag tgg atc aag aga cag att      868
Val Tyr Thr Ser Thr Ser His Phe Thr Gln Trp Ile Lys Arg Gln Ile
265                 270                 275                 280

ggc gac ctg aag ttt acc agc atg gct gtc ccc tcc ttc ctg agc cca      916
Gly Asp Leu Lys Phe Thr Ser Met Ala Val Pro Ser Phe Leu Ser Pro
                285                 290                 295

ttc atc ctc act ggc tac att ctg ctg gta tcc ttg ggc tcc ctg tgg      964
Phe Ile Leu Thr Gly Tyr Ile Leu Leu Val Ser Leu Gly Ser Leu Trp
            300                 305                 310

ctc ttg tgagctgtgt ttctataaca gccactccca gaggctactt ttccctcctc      1020
Leu Leu

tctgctccgc cctcagaaga cgtggacacc ggaggctgaa caggacttca ggacagaggg   1080

acttggggaa gggtccttga cccactgtgg gttttgttcc ccagttgttc aatgaagatg   1140

ctcttgaacc ttta                                                     1154


<210> SEQ ID NO 2
<211> LENGTH: 314
<212> TYPE: PRT
<213> ORGANISM: Mus musculus

<400> SEQUENCE: 2

Met Ala Cys Gly Ser Val Asp Pro His Gly Leu Leu Ser Ser Pro Leu
 1               5                  10                  15

Ala Ser Ala Arg Leu Asn Ser Leu Pro Tyr Met Glu Gly Pro Trp Ile
            20                  25                  30

Trp Ser Cys Gly Gln Thr Asn Ile Thr Cys Lys Val Val Asn Gly Lys
        35                  40                  45

Ala Val Glu Val Gly Lys Trp Pro Trp Gln Val Ser Ile Leu Phe Leu
    50                  55                  60

Gly Met Tyr Ile Cys Ser Gly Ser Leu Ile His His His Trp Ile Leu
65                  70                  75                  80

Thr Ala Ala His Cys Leu Gln Arg Ser Lys Asn Pro Ala Lys Tyr Thr
                85                  90                  95

Val Lys Val Gly Val Gln Thr Leu Pro Asp Asn Ser Thr Ser Glu Leu
            100                 105                 110

Leu Val Thr Arg Ile Val Ile His Glu Asn Phe Ile Asn Arg Met Ser
        115                 120                 125

Asp Asp Ile Ala Ile Leu Lys Leu Lys Tyr Pro Val Thr Trp Ser Pro
```

-continued

```
    130                 135                 140

Leu Val Gln Pro Ile Cys Leu Pro Ser Phe Asn Leu Lys Pro Ser Ile
145                 150                 155                 160

Gly Thr Met Cys Trp Val Val Gly Trp Gly Leu Glu Lys Ala Glu Gly
                165                 170                 175

His Pro Lys Thr Pro Tyr Ser Val Gln Gly Leu Ala Val Arg Ile Val
            180                 185                 190

Asn Asn Glu Ile Cys Asn His Arg Tyr Gln Phe Leu Leu Leu Lys Asn
        195                 200                 205

Gln Lys Lys Phe Ile Gly Asn Asp Met Leu Cys Thr Ser Ser Glu Trp
    210                 215                 220

Gly Leu Asp Thr Cys Gln Asp Thr Ser Gly Ser Ser Leu Val Cys Gln
225                 230                 235                 240

Met Asn Lys Thr Trp Val Gln Met Gly Val Val Ser Trp Asn Phe Asp
                245                 250                 255

Cys Gly Arg Arg Gln Phe Pro Ser Val Tyr Thr Ser Thr Ser His Phe
            260                 265                 270

Thr Gln Trp Ile Lys Arg Gln Ile Gly Asp Leu Lys Phe Thr Ser Met
        275                 280                 285

Ala Val Pro Ser Phe Leu Ser Pro Phe Ile Leu Thr Gly Tyr Ile Leu
    290                 295                 300

Leu Val Ser Leu Gly Ser Leu Trp Leu Leu
305                 310
```

<210> SEQ ID NO 3
<211> LENGTH: 942
<212> TYPE: DNA
<213> ORGANISM: Artificial Sequence
<220> FEATURE:
<223> OTHER INFORMATION: Degenerate polynucleotide sequence of mouse ztryp1 (SEQ ID NO:2)
<221> NAME/KEY: misc_feature
<222> LOCATION: (1)...(942)
<223> OTHER INFORMATION: n = A,T,C or G

<400> SEQUENCE: 3

```
atggcntgyg gnwsngtnga yccncayggn ytnytnwsnw snccnytngc nwsngcnmgn     60

ytnaaywsny tnccntayat ggarggnccn tggathtggw sntgyggnca racnaayath    120

acntgyaarg tngtnaaygg naargcngtn gargtnggna artggccntg gcargtnwsn    180

athytnttyy tnggnatgta yathtgywsn ggnwsnytna thcaycayca ytggathytn    240

acngcngcnc aytgyytnca rmgnwsnaar aayccngcna artayacngt naargtnggn    300

gtncaracny tnccngayaa ywsnacnwsn garytnytng tnacnmgnat hgtnathcay    360

garaayttya thaaymgnat gwsngaygay athgcnathy tnaarytnaa rtayccngtn    420

acntggwsnc cnytngtnca rccnathtgy ytnccnwsnt tyaayytnaa rccnwsnath    480

ggnacnatgt gytgggtngt nggntggggn ytngaraarg cngarggnca yccnaaracn    540

ccntaywsng tncarggnyt ngcngtnmgn athgtnaaya aygarathtg yaaycaymgn    600

taycarttyy tnytnytnaa raaycaraar aarttyathg gnaaygayat gytntgyacn    660

wsnwsngart ggggnytnga yacntgycar gayacnwsng gnwsnwsnyt ngtntgycar    720

atgaayaara cntgggtnca ratgggngtn gtnwsntgga ayttygaytg yggnmgnmgn    780

carttyccnw sngtntayac nwsnacnwsn cayttyacnc artggathaa rmgncarath    840

ggngayytna arttyacnws natggcngtn ccnwsnttyy tnwsnccntt yathytnacn    900
```

-continued

```
ggntayathy tnytngtnws nytnggnwsn ytntggytny tn                         942


<210> SEQ ID NO 4
<211> LENGTH: 22
<212> TYPE: DNA
<213> ORGANISM: Artificial Sequence
<220> FEATURE:
<223> OTHER INFORMATION: Oligonucleotide primer ZC18364

<400> SEQUENCE: 4

cccttcccca agtccctctg tc                                                22


<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer ZC18365

<400> SEQUENCE: 5

tggctgtccc ctccttcctg a                                                 21


<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer ZC9739

<400> SEQUENCE: 6

ccatcctaat acgactcact atagggc                                           27


<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer ZC9719

<400> SEQUENCE: 7

actcactata gggctcgagc ggc                                               23


<210> SEQ ID NO 8
<211> LENGTH: 22
<212> TYPE: DNA
<213> ORGANISM: Artificial Sequence
<220> FEATURE:
<223> OTHER INFORMATION: Oligonucleotide primer ZC20900

<400> SEQUENCE: 8

gatggcgatg tcgtcagaca tg                                                22


<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 9

caccagacat aatagctgac agact                                             25


<210> SEQ ID NO 10
<211> LENGTH: 21
<212> TYPE: DNA
<213> ORGANISM: Artificial Sequence
```

-continued

```
<220> FEATURE:
<223> OTHER INFORMATION: Oligonucleotide primer ZC5020

<400> SEQUENCE: 10

cactggagtg gcaacttcca g                                            21


<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer ZC20771

<400> SEQUENCE: 11

actggtaccg atgattgcag                                              20


<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer ZC22855

<400> SEQUENCE: 12

gagctggaac tttgactg                                                18


<210> SEQ ID NO 13
<211> LENGTH: 18
<212> TYPE: DNA
<213> ORGANISM: Artificial Sequence
<220> FEATURE:
<223> OTHER INFORMATION: Oligonucleotide primer ZC22856

<400> SEQUENCE: 13

gccatgctgg taaacttc                                                18


<210> SEQ ID NO 14
<211> LENGTH: 1171
<212> TYPE: DNA
<213> ORGANISM: Homo sapiens
<220> FEATURE:
<221> NAME/KEY: CDS
<222> LOCATION: (34)...(969)
<221> NAME/KEY: misc_feature
<222> LOCATION: (1)...(1171)
<223> OTHER INFORMATION: n = A,T,C or G

<400> SEQUENCE: 14

aggggagcat tgaggagtag atacccactt gcc atg gcc tgt ggg ccg ggg gat      54
                                     Met Ala Cys Gly Pro Gly Asp
                                      1               5

ctt caa agc ctt aca tct ccg ctt tcc tct gcc aga tta gat tat cag      102
Leu Gln Ser Leu Thr Ser Pro Leu Ser Ser Ala Arg Leu Asp Tyr Gln
         10                  15                  20

ccg tct att gaa ggg ccc tgg ctc cgg gcc tgc ggt cag acc aac gtg      150
Pro Ser Ile Glu Gly Pro Trp Leu Arg Ala Cys Gly Gln Thr Asn Val
     25                  30                  35

tcc tgc agg gtg gtg aag ggg aag ctg gta gag gta ggc aag tgg cca      198
Ser Cys Arg Val Val Lys Gly Lys Leu Val Glu Val Gly Lys Trp Pro
 40                  45                  50                  55

tgg cag gtg agc atc ctt ttc ctg ggc acg tac atc tgc agt ggc tcc      246
Trp Gln Val Ser Ile Leu Phe Leu Gly Thr Tyr Ile Cys Ser Gly Ser
                 60                  65                  70

ctc atc cac cac cag tgg gtc ctc acg gct gcg cac tgc ttg cag aga      294
Leu Ile His His Gln Trp Val Leu Thr Ala Ala His Cys Leu Gln Arg
```

-continued

```
            75                  80                  85

ttc aag gac ctc agc ctg tac tcc gtg atg gtg gga gtc cac cag cgc      342
Phe Lys Asp Leu Ser Leu Tyr Ser Val Met Val Gly Val His Gln Arg
         90                  95                 100

cca gaa aat agc act cag ctc ccg ctc act cgc atg gtg att cat aag      390
Pro Glu Asn Ser Thr Gln Leu Pro Leu Thr Arg Met Val Ile His Lys
    105                 110                 115

gat ttc agc aat ctc atg tct cag gac att gcc ctc cta aag ctc agg      438
Asp Phe Ser Asn Leu Met Ser Gln Asp Ile Ala Leu Leu Lys Leu Arg
120                 125                 130                 135

gac tcc atc tcg tgg tcc ccc ttc gtc cag cct gtc tgc ctc cct aac      486
Asp Ser Ile Ser Trp Ser Pro Phe Val Gln Pro Val Cys Leu Pro Asn
                140                 145                 150

atc aaa ttc aag cca tcc att gga agc atg tgc tgg gta atc ggc tgg      534
Ile Lys Phe Lys Pro Ser Ile Gly Ser Met Cys Trp Val Ile Gly Trp
            155                 160                 165

gga nnn nnn nnn nnn nnn nnn nnn nnn nnn nnn nnn nnn nnn nnn nnn      582
Gly Xaa Xaa Xaa Xaa Xaa Xaa Xaa Xaa Xaa Xaa Xaa Xaa Xaa Xaa Xaa
        170                 175                 180

nnn nnn nnn nnn nnn nnn nnn nnn nnn nnn nnn nnn nnn nnn nnn nnn      630
Xaa Xaa Xaa Xaa Xaa Xaa Xaa Xaa Xaa Xaa Xaa Xaa Xaa Xaa Xaa Xaa
    185                 190                 195

nnn nnn nnn nnn nnn nnn nnn nnn nnn nnn nnn nnn nnn nnn nnn nnn      678
Xaa Xaa Xaa Xaa Xaa Xaa Xaa Xaa Xaa Xaa Xaa Xaa Xaa Xaa Xaa Xaa
200                 205                 210                 215

nnn nnn nnn nnn nnn nnn nnn nnn nnn nnn nnn nnn nnn nnn nnn tct      726
Xaa Xaa Xaa Xaa Xaa Xaa Xaa Xaa Xaa Xaa Xaa Xaa Xaa Xaa Xaa Ser
                220                 225                 230

gga agc tcc ctt gtc tgc caa atg gac aag acc tgg att cag ata gga      774
Gly Ser Ser Leu Val Cys Gln Met Asp Lys Thr Trp Ile Gln Ile Gly
            235                 240                 245

gtg gta agc tgg agc ttt agt tgt ggc cag cgc cac ttc cca ggt atc      822
Val Val Ser Trp Ser Phe Ser Cys Gly Gln Arg His Phe Pro Gly Ile
        250                 255                 260

tac acc agc act gcc cac ttc aac cag tgg atc agg act gag gtt gct      870
Tyr Thr Ser Thr Ala His Phe Asn Gln Trp Ile Arg Thr Glu Val Ala
    265                 270                 275

aac ata agg ttc atc agt agg gct ggc cct gcc ttc ctg agc cca gtt      918
Asn Ile Arg Phe Ile Ser Arg Ala Gly Pro Ala Phe Leu Ser Pro Val
280                 285                 290                 295

ttc ctc act ggc tac att cta ctg ggc tcc ttg agc tcc ctg tgg ctc      966
Phe Leu Thr Gly Tyr Ile Leu Leu Gly Ser Leu Ser Ser Leu Trp Leu
                300                 305                 310

ctg tgagcggtgt ttcaaggaca gtccctccca gaggctgctt ctccctcccc          1019
Leu

tctgttctac cctcagaagt ggagacgaga ggttgcccag gatggcaggg cagagtgagg   1079

gggagggtcc gagagccact gttactttct gatgttcaat gaagatgctt ttgaacttta   1139

aaaaaaaaaa aaaaaaaaaa attggcggcc gc                                 1171
```

<210> SEQ ID NO 15
<211> LENGTH: 312
<212> TYPE: PRT
<213> ORGANISM: Homo sapiens
<220> FEATURE:
<221> NAME/KEY: VARIANT
<222> LOCATION: (1)...(312)
<223> OTHER INFORMATION: Xaa = Any Amino Acid

<400> SEQUENCE: 15

-continued

```
Met Ala Cys Gly Pro Gly Asp Leu Gln Ser Leu Thr Ser Pro Leu Ser
 1               5                  10                  15

Ser Ala Arg Leu Asp Tyr Gln Pro Ser Ile Glu Gly Pro Trp Leu Arg
            20                  25                  30

Ala Cys Gly Gln Thr Asn Val Ser Cys Arg Val Val Lys Gly Lys Leu
        35                  40                  45

Val Glu Val Gly Lys Trp Pro Trp Gln Val Ser Ile Leu Phe Leu Gly
    50                  55                  60

Thr Tyr Ile Cys Ser Gly Ser Leu Ile His His Gln Trp Val Leu Thr
65                  70                  75                  80

Ala Ala His Cys Leu Gln Arg Phe Lys Asp Leu Ser Leu Tyr Ser Val
                85                  90                  95

Met Val Gly Val His Gln Arg Pro Glu Asn Ser Thr Gln Leu Pro Leu
            100                 105                 110

Thr Arg Met Val Ile His Lys Asp Phe Ser Asn Leu Met Ser Gln Asp
        115                 120                 125

Ile Ala Leu Leu Lys Leu Arg Asp Ser Ile Ser Trp Ser Pro Phe Val
    130                 135                 140

Gln Pro Val Cys Leu Pro Asn Ile Lys Phe Lys Pro Ser Ile Gly Ser
145                 150                 155                 160

Met Cys Trp Val Ile Gly Trp Gly Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Ser Gly Ser Ser Leu Val Cys Gln Met Asp
225                 230                 235                 240

Lys Thr Trp Ile Gln Ile Gly Val Val Ser Trp Ser Phe Ser Cys Gly
                245                 250                 255

Gln Arg His Phe Pro Gly Ile Tyr Thr Ser Thr Ala His Phe Asn Gln
            260                 265                 270

Trp Ile Arg Thr Glu Val Ala Asn Ile Arg Phe Ile Ser Arg Ala Gly
        275                 280                 285

Pro Ala Phe Leu Ser Pro Val Phe Leu Thr Gly Tyr Ile Leu Leu Gly
    290                 295                 300

Ser Leu Ser Ser Leu Trp Leu Leu
305                 310
```

```
<210> SEQ ID NO 16
<211> LENGTH: 936
<212> TYPE: DNA
<213> ORGANISM: Artificial Sequence
<220> FEATURE:
<223> OTHER INFORMATION: Degenerate polynucleotide sequence of human
      ztryp1 (SEQ ID NO:15)
<221> NAME/KEY: misc_feature
<222> LOCATION: (1)...(936)
<223> OTHER INFORMATION: n = A,T,C or G

<400> SEQUENCE: 16

atggcntgyg gnccnggnga yytncarwsn ytnacnwsnc cnytnwsnws ngcnmgnytn     60

gaytaycarc cnwsnathga rggnccntgg ytnmgngcnt gyggncarac naaygtnwsn    120

tgymgngtng tnaarggnaa rytngtngar gtnggnaart ggccntggca rgtnwsnath    180
```

-continued

```
ytnttyytng gnacntayat htgywsnggn wsnytnathc aycaycartg ggtnytnacn    240

gcngcncayt gyytncarmg nttyaargay ytnwsnytnt aywsngtnat ggtnggngtn    300

caycarmgnc cngaraayws nacncarytn ccnytnacnm gnatggtnat hcayaargay    360

ttywsnaayy tnatgwsnca rgayathgcn ytnytnaary tnmgngayws nathwsntgg    420

wsnccnttyg tncarccngt ntgyytnccn aayathaart tyaarccnws nathggnwsn    480

atgtgytggg tnathggntg gggnnnnnnn nnnnnnnnnn nnnnnnnnnn nnnnnnnnnn    540

nnnnnnnnnn nnnnnnnnnn nnnnnnnnnn nnnnnnnnnn nnnnnnnnnn nnnnnnnnnn    600

nnnnnnnnnn nnnnnnnnnn nnnnnnnnnn nnnnnnnnnn nnnnnnnnnn nnnnnnnnnn    660

nnnnnnnnnn nnnnnnnnnn nnnnnnnnnn wsnggnwsnw snytngtntg ycaratggay    720

aaracntgga thcarathgg ngtngtnwsn tggwsnttyw sntgyggnca rmgncaytty    780

ccnggnatht ayacnwsnac ngcncaytty aaycartgga thmgnacnga rgtngcnaay    840

athmgnttya thwsnmgngc nggnccngcn ttyytnwsnc cngtnttyyt nacnggntay    900

athytnytng gnwsnytnws nwsnytntgg ytnytn                              936
```

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide primer ZC21195

<400> SEQUENCE: 17
gaggagacca taacccccga cag 23

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide primer ZC21196

<400> SEQUENCE: 18
catagctccc accacacgat ttt 23

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 19
caccagacat aatagctgac agact 25

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide primer ZC17574

<400> SEQUENCE: 20
ggtrttgctc agcatgcaca c 21

<210> SEQ ID NO 21
<211> LENGTH: 24
<212> TYPE: DNA

-continued

<213> ORGANISM: Artificial Sequence
<220> FEATURE:
<223> OTHER INFORMATION: Oligonucleotide primer ZC17600

<400> SEQUENCE: 21
catgtaggcc atgaggtcca ccac 24

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer ZC28936

<400> SEQUENCE: 22
cctccctaac atcaaattca agcc 24

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer ZC28937

<400> SEQUENCE: 23
tccaggtctt gtccatttgg caga 24

<210> SEQ ID NO 24
<211> LENGTH: 233
<212> TYPE: PRT
<213> ORGANISM: Artificial Sequence
<220> FEATURE:
<223> OTHER INFORMATION: Exemplary human/mouse ztryp1 fusion polypeptide

<400> SEQUENCE: 24

```
Val Val Lys Gly Lys Leu Val Glu Val Gly Lys Trp Pro Trp Gln Val
 1               5                  10                  15

Ser Ile Leu Phe Leu Gly Thr Tyr Ile Cys Ser Gly Ser Leu Ile His
            20                  25                  30

His Gln Trp Val Leu Thr Ala Ala His Cys Leu Gln Arg Phe Lys Asp
        35                  40                  45

Leu Ser Leu Tyr Ser Val Met Val Gly Val His Gln Arg Pro Glu Asn
    50                  55                  60

Ser Thr Gln Leu Pro Leu Thr Arg Met Val Ile His Lys Asp Phe Ser
65                  70                  75                  80

Asn Leu Met Ser Gln Asp Ile Ala Leu Leu Lys Leu Arg Asp Ser Ile
                85                  90                  95

Ser Trp Ser Pro Phe Val Gln Pro Val Cys Leu Pro Asn Ile Lys Phe
            100                 105                 110

Lys Pro Ser Ile Gly Ser Met Cys Trp Val Ile Gly Trp Gly Leu Glu
        115                 120                 125

Lys Ala Glu Gly His Pro Lys Thr Pro Tyr Ser Val Gln Gly Leu Ala
    130                 135                 140

Val Arg Ile Val Asn Asn Glu Ile Cys Asn His Arg Tyr Gln Phe Leu
145                 150                 155                 160

Leu Leu Lys Asn Gln Lys Lys Phe Ile Gly Asn Asp Met Leu Cys Thr
                165                 170                 175

Ser Ser Glu Trp Gly Leu Asp Thr Cys Gln Asp Thr Ser Gly Ser Ser
            180                 185                 190

Leu Val Cys Gln Met Asp Lys Thr Trp Ile Gln Ile Gly Val Val Ser
```

-continued

```
        195                 200                 205

Trp Ser Phe Ser Cys Gly Gln Arg His Phe Pro Gly Ile Tyr Thr Ser
    210                 215                 220

Thr Ala His Phe Asn Gln Trp Ile Arg
225                 230
```

TRYPTASE-LIKE POLYPEPTIDE ZTRYP1

REFERENCE TO RELATED APPLICATION

This application is related to Provisional Application No. 60/149,563, filed on Aug. 18, 1999. Under 35 U.S.C. § 119(e)(1), this application claims benefit of said Provisional Application.

BACKGROUND OF THE INVENTION

Human tryptase is a serine protease with trypsin-like proteolytic activity. For a general review see Numerof, R. P. et al., *Exp. Opin. Invest. Drugs* 6:811–817, 1997; Chan, H. et al., *Prot. Express. Purif.* 15:251–257, 1999; Elrod, K. C., and Numerof, R. P., *Emerging Therapeutic Targets* 3:203–212, 1999; and Clark, J. M. et al., *Drugs of the Future* 21:811–816, 1996. There are at least 2 genes for tryptase in the human genome that encode α-tryptase and β-tryptase which are about 93% identical. Human tryptase has a tetrameric structure that requires heparin for stability. Each of the subunits are catalytically active.

Human tryptase is almost exclusively found in the secretory granules of mast cells and is released along with heparin and histamine upon mast cell activation in inflammatory response. Mast cells containing tryptase have been identified in lung, gut mucosa, and skin mast cells. Human tryptase has been established as an important mediator of airway response and is implicated in increasing the magnitude of broncoconstriction in asthma. Tryptase has neuropeptidase activity that may directly induce asthmatic response by degrading broncoactive neuropeptides having broncodilatory activities hence increasing broncoconstriction. Neuropeptides cleaved by tryptase include vasoactive intestinal peptide (VIP), and peptide histidine methionine (PHM). In addition, tryptase has been shown to stimulate cytokine production, and exhibit mitogenic effects in a variety of cell types including human and rat lung fibroblasts, human bronchial epithelial cells, and dog airway smooth muscle cells and hence may also contribute to the hyperplasia and fibrotic changes observed in diseases such as asthma. Moreover, tryptase inhibitors have been found effective in reducing asthmatic response to exposure of antigen in animal models (allergic sheep) and in human trials, and in blocking the mitogenic effects described above.

Human tryptase has been implicated in other activities such as cleaving fibrinogen α and β chains, collagen IV, gelatinase and fibronectin. As such it is implicated in inhibition of coagulation and in tissue remodeling in the lung and other tissues. In addition, tryptase is shown to cleave calcitonin gene-related peptide (CGRP) which is a potent vasodilator and hence may potentiate gastric ulceration or increase cutaneous neurogenic inflammation, and promote smooth muscle contraction. In addition, tryptases are implicated in matrix degradation, wound healing and tumor metastasis.

There is a continuing need to discover new tryptase homologs, related serine proteases, and the like. The in vivo activity of human tryptase illustrates the enormous clinical potential of, and need for, related polypeptides, their agonists, and antagonists. The present invention provides such polypeptides for these and other uses that should be apparent to those skilled in the art from the teachings herein.

SUMMARY OF THE INVENTION

Within one aspect, the present invention provides an isolated polynucleotide encoding a serine protease polypeptide comprising a sequence of amino acid residues that is at least 90% identical to an amino acid sequence selected from the group consisting of: (a) the amino acid sequence as shown in SEQ ID NO:2 from amino acid number 44 (Val) to amino acid number 276 (Ile); (b) the amino acid sequence as shown in SEQ ID NO:15 from amino acid number 43 (Val) to amino acid number 275 (Arg); (c) the amino acid sequence as shown in SEQ ID NO:2 from amino acid number 24 (Leu) to amino acid number 276 (Ile); (d) the amino acid sequence as shown in SEQ ID NO:15 from amino acid number 19 (Arg) to amino acid number 275 (Arg); (e) the amino acid sequence as shown in SEQ ID NO:2 from amino acid number 44 (Val) to amino acid number 314 (Leu); (f) the amino acid sequence as shown in SEQ ID NO:15 from amino acid number 43 (Val) to amino acid number 312 (Leu); (g) the amino acid sequence as shown in SEQ ID NO: 2 from amino acid number 24 (Leu) to amino acid number 314 (Leu); (h) the amino acid sequence as shown in SEQ ID NO: 15 from amino acid number 19 (Arg) to amino acid number 312 (Leu); (i) the amino acid sequence as shown in SEQ ID NO:2 from amino acid number 1 (Met) to amino acid number 314 (Leu), (j) the amino acid sequence as shown in SEQ ID NO:15 from amino acid number 1 (Met) to amino acid number 312 (Leu), and (k) the amino acid sequence as shown in SEQ ID NO:24; and wherein the amino acid percent identity is determined using a FASTA program with ktup=1, gap opening penalty=10, gap extension penalty=1, and substitution matrix=BLOSUM62, with other parameters set as default. In one embodiment, the isolated polynucleotide disclosed above encodes a serine protease polypeptide that comprises a sequence of amino acid residues an amino acid sequence selected from the group consisting of: (a) the amino acid sequence as shown in SEQ ID NO:2 from amino acid number 44 (Val) to amino acid number 276 (Ile); (b) the amino acid sequence as shown in SEQ ID NO:15 from amino acid number 43 (Val) to amino acid number 275 (Arg);.(c) the amino acid sequence as shown in SEQ ID NO:2 from amino acid number 24 (Leu) to amino acid number 276 (Ile); (d) the amino acid sequence as shown in SEQ ID NO:15 from amino acid number 19 (Arg) to amino acid number 275 (Arg); (e) the amino acid sequence as shown in SEQ ID NO:2 from amino acid number 44 (Val) to amino acid number 314 (Leu); (f) the amino acid sequence as shown in SEQ ID NO: 15 from amino acid number 43 (Val) to amino acid number 312 (Leu); (g) the amino acid sequence as shown in SEQ ID NO: 2 from amino acid number 24 (Leu) to amino acid number 314 (Leu); (h) the amino acid sequence as shown in SEQ ID NO: 15 from amino acid number 19 (Arg) to amino acid number 312 (Leu); (i) the amino acid sequence as shown in SEQ ED NO:2 from amino acid number 1 (Met) to amino acid number 314 (Leu), (j) the amino acid sequence as shown in SEQ ID NO:15 from amino acid number 1 (Met) to amino acid number 312 (Leu), and (k) the amino acid sequence as shown in SEQ ID NO:24. In another embodiment, the isolated polynucleotide disclosed above encodes a serine protease polypeptide that has protease activity. In another embodiment, the isolated polynucleotide disclosed above encodes a serine protease polypeptide consisting of a sequence of amino acid residues as shown in SEQ ID NO:2 from amino acid number 44 (Val) to amino acid number 276 (Ile) or of a sequence of amino acid residues as shown in SEQ ID NO: 15 from amino acid number 43 (Val) to amino acid number 275 (Arg).

Within a second aspect, the present invention provides an expression vector comprising the following operably linked elements: a transcription promoter; a DNA segment encoding a serine protease polypeptide with an amino acid sequence consisting of: (a) the amino acid sequence as shown in SEQ ID NO:2 from amino acid number 44 (Val) to amino acid number 276 (Ile); (b) the amino acid sequence as shown in SEQ ID NO:15 from amino acid number 43 (Val) to amino acid number 275 (Arg); (c) the amino acid sequence as shown in SEQ ID NO:2 from amino acid number 24 (Leu) to amino acid number 314 (Leu); (d) the amino acid sequence as shown in SEQ ID NO:15 from amino acid number 19 (Arg) to amino acid number 312 (Leu); and (e) the amino acid sequence as shown in SEQ ID NO:24; and a transcription terminator. Within one embodiment, the expression vector disclosed above further comprises a secretory signal sequence operably linked to the DNA segment.

Within a third aspect, the present invention provides a cultured cell into which has been introduced an expression vector as disclosed above, wherein the cell expresses a polypeptide encoded by the DNA segment.

Within another aspect, the present invention provides a DNA construct encoding a fusion protein, the DNA construct comprising: a first DNA segment encoding a polypeptide that is selected from the group consisting of: (a) the amino acid sequence of SEQ ID NO: 2 from residue number 1 (Met), to residue number 23 (Ser); (b) the amino acid sequence of SEQ ID NO: 15 from residue number 1 (Met), to residue number 18 (Ala); (c) the amino acid sequence of SEQ ID NO: 2 from residue number 24 (Leu), to residue number 43 (Lys); (d) the amino acid sequence of SEQ ID NO: 15 from residue number 19 (Arg), to residue number 42 (Arg); (e) the amino acid sequence of SEQ ID NO: 2 from residue number 24 (Leu), to residue number 276 (Ile); (f) the amino acid sequence of SEQ ID NO: 15 from residue number 19 (Arg), to residue number 275 (Arg); (g) the amino acid sequence of SEQ ID NO: 2 from residue number 24 (Leu), to residue number 314 (Leu); (h) the amino acid sequence of SEQ ID NO:15 from residue number 19 (Arg), to residue number 312 (Leu); (9) the amino acid sequence of SEQ ID NO: 2 from residue number 44 (Val), to residue number 276 (Ile); (j) the amino acid sequence of SEQ ID NO: 15 from residue number 43 (Val), to residue number 275 (Arg); (k) the amino acid sequence of SEQ ID NO: 2 from residue number 44 (Val), to residue number 314 (Leu); (1) the amino acid sequence of SEQ ID NO: 15 from residue number 43 (Val), to residue number 312 (Leu); (m) the amino acid sequence of SEQ ID NO: 2 from residue number 277 (Lys), to residue number 314 (Leu); (n) the amino acid sequence of SEQ ID NO:15 from residue number 276 (Thr), to residue number 312 (Leu); and (o) the amino acid sequence of SEQ ID NO:24; and at least one other DNA segment encoding an additional polypeptide, wherein the first and other DNA segments are connected in-frame; and encode the fusion protein.

Within another aspect, the present invention provides a fusion protein produced by a method comprising: culturing a host cell into which has been introduced a vector comprising the following operably linked elements: (a) a transcriptional promoter; (b) a DNA construct encoding a fusion protein as disclosed above; and (c) a transcriptional terminator; and recovering the protein encoded by the DNA segment.

Within another aspect, the present invention provides an isolated polypeptide comprising a sequence of amino acid residues that is at least 90% identical to an amino acid sequence selected from the group consisting of: (a) the amino acid sequence as shown in SEQ ID NO:2 from amino acid number 44 (Val) to amino acid number 276 (Ile); (b) the amino acid sequence as shown in SEQ ID NO:15 from amino acid number 43 (Val) to amino acid number 275 (Arg); (c) the amino acid sequence as shown in SEQ ID NO:2 from amino acid number 24 (Leu) to amino acid number 276 (Ile); (d) the amino acid sequence as shown in SEQ ID NO: 15 from amino acid number 19 (Arg) to amino acid number 275 (Arg); (e) the amino acid sequence as shown in SEQ ID NO:2 from amino acid number 44 (Val) to amino acid number 314 (Leu); (f) the amino acid sequence as shown in SEQ ID NO:15 from amino acid number 43 (Val) to amino acid number 312 (Leu); (g) the amino acid sequence as shown in SEQ ID NO: 2 from amino acid number 24 (Leu) to amino acid number 314 (Leu); (h) the amino acid sequence as shown in SEQ ID NO: 15 from amino acid number 19 (Arg) to amino acid number 312 (Leu); (i) the amino acid sequence as shown in SEQ ID NO:2 from amino acid number 1 (Met) to amino acid number 314 (Leu), (j) the amino acid sequence as shown in SEQ ID NO:15 from amino acid number 1 (Met) to amino acid number 312 (Leu), and (k) the amino acid sequence as shown in SEQ ID NO:24; and wherein the amino acid percent identity is determined using a FASTA program with ktup=1, gap opening penalty=10, gap extension penalty=1, and substitution matrix=BLOSUM62, with other parameters set as default. In one embodiment, the isolated polypeptide disclosed above comprises a sequence of amino acid residues selected from the group consisting of: (a) the amino acid sequence as shown in SEQ ID NO:2 from amino acid number 44 (Val) to amino acid number 276 (Ile); (b) the amino acid sequence as shown in SEQ ID NO:15 from amino, acid number 43 (Val) to amino acid number 275 (Arg); (c) the amino acid sequence as shown in SEQ ID NO:2 from amino acid number 24 (Leu) to amino acid number. 276 (Ile); (d) the amino acid sequence as shown in SEQ ID NO:15 from amino acid number 19 (Arg) to amino acid number 275 (Arg); (e) the amino acid sequence as shown in SEQ ID NO:2 from amino acid number 44 (Val) to amino acid number 314 (Leu); (f) the amino acid sequence as shown in SEQ ID NO:15 from amino acid number 43 (Val) to amino acid number 312 (Leu); (g) the amino acid sequence as shown in SEQ ID NO: 2 from amino acid number 24 (Leu) to amino acid number 314 (Leu); (h) the amino acid sequence as shown in SEQ ID NO: 15 from amino acid number 19 (Arg) to amino acid number 312 (Leu); (i) the amino acid sequence as shown in SEQ ID NO:2 from amino acid number 1 (Met) to amino acid number 314 (Leu), (j) the amino acid sequence as shown in SEQ ID NO:15 from amino acid number 1 (Met) to amino acid number 312 (Leu), and (k) the amino acid sequence as shown in SEQ ID NO:24. In another embodiment, the isolated polypeptide disclosed above has protease activity. In another embodiment, the isolated polypeptide disclosed above has a sequence of amino acid residues is as shown in SEQ ID NO:2 from amino acid number 44 (Val) to amino acid number 276 (Ile), or the sequence of amino acids is as shown in SEQ ID NO:15 from amino acid number 43 (Val) to amino acid number 275 (Arg).

Within another aspect, the present invention provides a method of producing a serine protease polypeptide comprising: culturing a cell as disclosed above; and isolating the serine protease polypeptide produced by the cell.

Within another aspect, the present invention provides a method of producing an antibody to serine protease polypeptide comprising: inoculating an animal with a polypeptide selected from the group consisting of: (a) a polypeptide consisting of 9 to 232 amino acids, wherein the polypeptide is a contiguous sequence of amino acids in SEQ ID NO:2 from amino acid number 44 (Val) to amino acid number 276 (Ile); (b) a polypeptide consisting of 9 to 233 amino acids, wherein the polypeptide is a contiguous sequence of amino acids in SEQ ID NO: 15 from amino acid number 43 (Val) to amino acid number 275 (Arg), excluding the sequence in SEQ ID NO:15 from amino acid number 169 to 230; (c) a polypeptide as disclosed above; (d) a polypeptide comprising an amino acid sequence from residue number 125 (Asn) to residue number 130 (Asp) of SEQ ID NO:2; (e) a polypeptide comprising an amino acid sequence from residue number 177 (His) to residue number 172 (Glu) of SEQ ID NO:2; (f) a polypeptide comprising an amino acid sequence from residue number 256 (Asp) to residue number 261 (Gln) of SEQ ID NO:2; (g) a polypeptide comprising an amino acid sequence from residue number 277 (Lys) to residue number 282 (Asp) of SEQ ID NO:2; (h) a polypeptide comprising an amino acid sequence from residue number 117 (Gln) to amino acid number 122 (Ser) of SEQ ID NO: 15; (i) a polypeptide comprising an amino acid sequence from residue number 57 (Arg) to amino acid number 62 (Lys) of SEQ ID NO:15; (j) a polypeptide comprising an amino acid sequence from residue number 116 (His) to amino acid number 121 (Asn) of SEQ ID NO: 15; and (k) a polypeptide comprising an amino acid sequence from residue number 147 (Lys) to amino acid number 152 (Ser) of SEQ ID NO:15; and wherein the polypeptide elicits an immune response in the animal to produce the antibody; and isolating the antibody from the animal.

Within another aspect, the present invention provides an antibody produced by the method as disclosed above, which binds to a serine protease polypeptide. In one embodiment, the antibody disclosed above is a monoclonal antibody. Within another aspect, the present invention provides an antibody that specifically binds to a polypeptide as disclosed above.

These and other aspects of the invention will become evident upon reference to the following detailed description of the invention.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5'ATGCACGGG 3' is complementary to 5'CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and EL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides novel serine protease polypeptides and proteins. The novel serine protease, termed ztryp1 was discovered and identified to be a novel tryptase by the presence of polypeptide and polynucleotide features characteristic of tryptases (e.g., α- and β-tryptases).

The sequence of each the human and mouse ztryp1 polypeptide was obtained from a clone believed to contain its corresponding polynucleotide sequence. Libraries that might be searched for such sequences include testis, heart, lung, and the like.

The nucleotide sequence of a representative mouse ztryp1-encoding DNA is described in SEQ ID NO:1, and its deduced 314 amino acid sequence is described in SEQ ID NO:2. In its entirety, the ztryp1 polypeptide (SEQ ID NO:2) represents a full-length polypeptide segment (pre-pro-polypeptide) (residue 1 (Met) to residue 314 (Leu) of SEQ ID NO:2). The domains and structural features of ztryp1 are further described below.

Analysis of the ztryp1 pre-pro-polypeptide encoded by the DNA sequence of SEQ ID NO:1 revealed an open reading frame encoding 314 amino acids (SEQ ID NO:2) comprising a predicted signal peptide of 23 amino acid residues (residue 1 (Met) to residue 23 (Ser) of SEQ ID NO:2), and a pro-polypeptide (or pro-protein) of 291 amino acids (residue 24 (Leu) to residue 314 (Leu) of SEQ ID NO:2); The Ztryp1 pro-protein has an unglycosylated molecular weight of approximately 33,005 Daltons (D). Further analysis of SEQ ID NO:2 indicates the presence of the following structural regions and features:

1) A pro-peptide from residue 24 (Leu) to residue 43 (Lys) is present, which when cleaved generates a mature ztryp1 polypeptide corresponding to residue 44 (Val) to residue 314 (Leu) of SEQ ID NO:2. Within the mature ztryp1 polypeptide is a transmembrane domain at the C-terminus (from approximately residue 293 (Phe) to residue 314 (Leu)). Also within the mature ztryp1 polypeptide is a dibasic Lys-Arg cleavage site at residues 277 and 278, which upon cleavage generates a 232 amino acid residue active ztryp1 polypeptide corresponding from residue 44 (Val) to residue 276 (Ile) of SEQ ID NO:2. This ztryp1 active polypeptide has an unglycosylated molecular weight of approximately 26,685 Daltons (D).

2) The active ztryp1 polypeptide contains critical active site residues typical of serine proteases at $His_{84}$, $Asp_{130}$, and $Ser_{233}$ (as shown in SEQ ID NO:2). Moreover, the active ztryp1 polypeptide contains a binding pocket comprising residues 221 (Ser) to 227 (Asp) and residues 254 (Asn) to 267 (Thr) of SEQ ID NO:2. Within the binding pocket the presence of $Asp_{227}$ indicates that the ztryp1 active polypeptide is trypsin-like in its enzymatic specificity.

3) The active ztryp1 polypeptide further contains two N-linked glycosylation sites at residues 107 (Asn) to 109 (Thr) and residues 242 (Asn) to 244 (Thr) of SEQ ID NO:2. Similar N-linked glycosylation sites are seen in elastase and dog tryptase.

The nucleotide sequence of a representative human ztryp1-encoding DNA is described in SEQ ID NO:14, and its deduced 312 amino acid sequence is described in SEQ ID NO:15. In its entirety, the ztryp1 polypeptide (SEQ ID NO:15) represents a full-length polypeptide segment (pre-pro-polypeptide) (residue 1 (Met) to residue 312 (Leu) of SEQ ID NO:15). The domains and structural features of ztryp1 are further described below.

Analysis of the ztryp1 pre-pro-polypeptide encoded by the DNA sequence of SEQ ID NO: 14 revealed an open reading frame encoding 312 amino acids (SEQ ID NO:15) comprising a predicted signal peptide of 18 amino acid residues (residue 1 (Met) to residue 18 (Ala) of SEQ ID NO: 15), and a pro-polypeptide (or pro-protein) of 294 amino acids (residue 19 (Arg) to residue 312 (Leu) of SEQ ID NO:15). The Ztryp1 pro-protein has an unglycosylated molecular weight of approximately 32–24 kiloDaltons (kD). Further analysis of SEQ ID NO: 15 indicates the presence of the following structural regions and features:

1) A pro-peptide from residue 19 (Arg) to residue 42 (Arg) is present, which when cleaved generates a mature ztryp1 polypeptide corresponding to residue 43 (Val) to residue 312 (Leu) of SEQ ID NO:15. Within the mature ztryp1 polypeptide is a transmembrane domain at the C-terminus (from approximately residue 291 (Phe) to residue 312 (Leu)). Also within the mature ztryp1 polypeptide is a cleavage site at residues 275, which upon cleavage generates a 233 amino acid residue active ztryp1 polypeptide corresponding from residue 43 (Val) to residue 275 (Arg) of SEQ ID NO:15. This mature ztryp1 active polypeptide has an unglycosylated molecular weight of approximately 26–28 kD. The mature ztryp1 polypeptide can be made in an active soluble form corresponding from approximately residue 43 (Val) to residue 275 (Arg) of SEQ ID NO: 15.

2) The active ztryp1 polypeptide contains critical active site residues typical of serine proteases at $His_{83}$, $Asp_{128}$, and $Ser_{231}$ (as shown in SEQ ID NO:15). Moreover, within preferred embodiments the ztryp1 polypeptide contains an Asp at residue 225+/−2 (as shown in SEQ ID NO:15) wherein when the mouse ztryp1 and human ztryp1 amino acid sequences are optimally aligned, the mouse residue 227 (Asp) corresponds to the Asp in the human sequence. Moreover, within more preferred embodiments, this critical Asp residue is within a binding pocket of about 7 residues comprising residues 219+/−2 to 225+/−2 (Asp) and about 14 residues 252+/−2 to 265+/−2 of SEQ ID NO:15. Within the binding pocket the presence of the critical Asp residue described above indicates that the ztryp1 active polypeptide is trypsin-like in its enzymatic specificity.

3) The active ztryp1 polypeptide further contains two N-linked glycosylation sites at residues 106 (Asn) to 108 (Thr) of SEQ ID NO:15. A similar N-linked glycosylation site is seen in elastase and dog tryptase.

The corresponding polynucleotides encoding the ztryp1 polypeptide regions, domains, motifs, residues and sequences described above are as shown in SEQ ID NO:1 or SEQ ID NO:14.

The highly conserved amino acids in the ztryp1 active polypeptide can be used as a tool to identify new family members. For instance, reverse transcription-polymerase chain reaction (RT-PCR) can be used to amplify sequences encoding the conserved binding pocket and active site residues from RNA obtained from a variety of tissue sources or cell lines. In particular, highly degenerate primers designed from the ztryp1 sequences are useful for this purpose.

The present invention also provides polynucleotide molecules, including DNA and RNA molecules that encode the ztryp1 polypeptides disclosed herein. Those skilled in the art will readily recognize that, in view of the degeneracy of the genetic code, considerable sequence variation is possible among these polynucleotide molecules. SEQ ID NO:3 and SEQ ID NO:16 is a degenerate DNA sequence that encompasses all DNAs that encode the ztryp1 polypeptide of SEQ ID NO:2 and SEQ ID NO:15 respectively. Those skilled in the art will recognize that the degenerate sequence of SEQ ID NO:3 and SEQ ID NO:16 also provides all RNA sequences encoding SEQ ID NO:2 or SEQ ID NO:15 by substituting U for T. Thus, ztryp1 polypeptide-encoding polynucleotides comprising nucleotide 1 to nucleotide 942 of SEQ ID NO:3, and ztryp1 polypeptide-encoding polynucleotides comprising nucleotide 1 to nucleotide 942 of SEQ ID NO:16, and their RNA equivalents are contemplated by the present invention. Table 1 sets forth the one-letter codes used within SEQ ID NO:3 and SEQ ID NO:16 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |

TABLE 1-continued

| Nucleotide | Resolution | Complement | Resolution |
|---|---|---|---|
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|C\|G\|T | H | A\|C\|T |
| N | A\|C\|G\|T | N | A\|C\|G\|T |

The degenerate codons used in SEQ ID NO:3 and SEQ ID NO:16, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2 or SEQ ID NO: 15. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 or SEQ ID NO:16 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1 or SEQ ID NO:14, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences (e.g., >50 base pairs) is performed at temperatures of about 20–25° C. below the calculated $T_m$. For smaller probes (e.g., >50 base pairs) hybridization is typically carried out at the $T_m$ or 5–10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40–50% formamide, up to about 6×SSC, about 5×Denhardt's solution, zero up to about 10% dextran sulfate, and about 10–20 μg/ml denatured commercially-available carrier DNA. Generally, such stringent conditions include temperatures of 20–70° C. and a hybridization buffer containing up to 6×SSC and 0–50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of ztryp1 RNA. Such tissues and cells are identified by Northern blotting (Thomas, *Proc. Natl. Acad. Sci. USA* 77:5201, 1980), and include testis, including whole testis tissue extracts or testicular cells, such as Sertoli cells, Leydig cells, spermatogonia, or epididymis, cells from vas deferens, and cervical cells, although DNA may also be prepared using RNA from other tissues, such as heart, lung, or gastrointestinal tissues, or isolated as genomic DNA. Total RNA can be prepared using guanidinium isothiocyanate extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–12, 1972). Complementary DNA (cDNA) is prepared from poly$(A)^+$ RNA using known methods. In the alternative, genomic DNA can be isolated. Polynucleotides encoding ztryp1 polypeptides are then identified and isolated by, for example, hybridization or PCR.

A full-length clone encoding ztryp1 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to ztryp1, receptor fragments, or other specific binding partners.

Ztryp1 polynucleotide sequences disclosed herein can also be used as probes or primers to clone 5' non-coding regions of a ztryp1 gene. In view of the tissue-specific expression observed for ztryp1 by Northern blotting, this gene region is expected to provide for testis-specific expression. Promoter elements from a ztryp1 gene could thus be used to direct the tissue-specific expression of heterologous genes in, for example, transgenic animals or patients treated with gene therapy. Cloning of 5' flanking sequences also facilitates production of ztryp1 proteins by "gene activation" as disclosed in U.S. Pat. No. 5,641,670. Briefly, expression of an endogenous ztryp1 gene in a cell is altered by introducing into the ztryp1 locus a DNA construct comprising at least a targeting sequence, a regulatory sequence, an exon, and an unpaired splice donor site. The targeting sequence is a ztryp1 5' non-coding sequence that permits homologous recombination of the construct with the endogenous ztryp1 locus, whereby the sequences within the construct become operably linked with the endogenous ztryp1 coding sequence. In this way, an endogenous ztryp1 promoter can be replaced or supplemented with other regulatory sequences to provide enhanced, tissue-specific, or otherwise regulated expression.

The polynucleotides of the present invention can also be synthesized using DNA synthesis machines. If chemically synthesized double stranded DNA is required for an application such as the synthesis of a DNA or a DNA fragment, then each complementary strand is made separately, for example via the phosphoramidite method known in the art. The production of short polynucleotides (60 to 80 bp) is technically straightforward and can be accomplished by synthesizing the complementary strands and then annealing them. However, for producing longer polynucleotides (longer than about 300 bp), special strategies are usually employed. For example, synthetic DNAs (double-stranded) are assembled in modular form from single-stranded fragments that are from 20 to 100 nucleotides in length. One method for building a synthetic DNA involves producing a set of overlapping, complementary oligonucleotides. Each internal section of the DNA has complementary 3' and 5' terminal extensions designed to base pair precisely with an adjacent section. After the DNA is assembled, the process is completed by ligating the nicks along the backbones of the two strands. In addition to the protein coding sequence, synthetic DNAs can be designed with terminal sequences that facilitate insertion into a restriction endonuclease site of a cloning vector. Alternative ways to prepare a full-length DNA are also known in the art. See Glick and Pasternak, *Molecular; Biotechnology, Principles & Applications of Recombinant DNA*, (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are ztryp1 polypeptides from other mammalian species, including human, porcine, ovine, bovine, canine, feline, equine, and other primate polypeptides. Orthologs of ztryp1 can be cloned using information and compositions provided by the present invention in combination with conventional cloning techniques. For example, a cDNA can be cloned using mRNA obtained from a tissue or cell type that expresses ztryp1 as disclosed herein. Suitable sources of mRNA can be identified by probing Northern blots with probes designed from the sequences disclosed herein. A library is then prepared from mRNA of a positive tissue or cell line. A ztryp1-encoding cDNA can then be isolated by a variety of methods, such as by probing with a complete or partial human cDNA or with one or more sets of degenerate probes based on the disclosed sequences. A cDNA can also be cloned using the polymerase chain reaction (PCR) (Mullis, U.S. Pat. No. 4,683,202), using primers designed from the representative ztryp1 sequences disclosed herein. Within an additional method, the cDNA library can be used to transform or transfect host cells, and expression of the cDNA of interest can be detected with an antibody to ztryp1 polypeptide. Similar techniques can also be applied to the isolation of genomic clones.

Those skilled in the art will recognize that the sequence disclosed in SEQ ID NO:1 or SEQ ID NO:14 represents a single allele of ztryp1 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1 or SEQ ID NO:14, including those containing silent mutations and those in which mutations result in amino acid sequence changes, are within the scope of the present invention, as are proteins which are allelic variants of SEQ ID NO:2 or SEQ ID NO:15. cDNAs generated from alternatively spliced mRNAs, which retain the properties of the ztryp1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated ztryp1 polypeptides that are substantially homologous to the polypeptides of SEQ ID NO:2 or SEQ ID NO:15 and their orthologs. The term "substantially homologous" is used herein to denote polypeptides having 70%, preferably 80%, more preferably at least 85%, sequence identity to the sequences shown in SEQ ID NO:2 or SEQ ID NO:15 or their orthologs. Such polypeptides will more preferably be at least 90% identical, and most preferably 95% or more identical to SEQ ID NO:2 or SEQ ID NO:15 or its orthologs.) Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\left[\begin{array}{c}\text{length of the longer sequence plus the}\\ \text{number of gaps introduced into the longer}\\ \text{sequence in order to align the two sequences}\end{array}\right]}\times 100$$

Briefly, FASTA first characterizes sequence similarity by identifying regions shared by the query sequence (e.g., SEQ ID NO:2 or SEQ ID NO:15) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol., supra.*

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant ztryp1. The FASTA algorithm is described by Pearson and Lipman, *Proc. Nat'l Acad. Sci. USA* 85:2444 (1988), and by Pearson, *Meth. Enzymol.* 183:63 (1990).

The BLOSUM62 table (Table 3) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant ztryp1 polypeptides or substantially homologous ztryp1 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from about 200 to 345 amino acid residues that comprise a sequence that is at least 90%, preferably at least 95%, and more preferably 99% or more identical to the corresponding region of SEQ ID NO:2 or SEQ ID NO:15. Polypeptides comprising affinity tags can further comprise a proteolytic cleavage site between the ztryp1 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions.

For example, a ztryp1 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-ztryp1 polypeptide fusions can be expressed in genetically engineered cells to produce a variety of multimeric ztryp1 analogs. Auxiliary domains can be fused to ztryp1 polypeptides to target them to specific cells, tissues, or macromolecules (e.g., collagen). For example, a ztryp1 polypeptide or protein could be targeted to a predetermined cell type by fusing a ztryp1 polypeptide to a ligand that specifically binds to a receptor on the surface of the target cell. In this way, polypeptides and proteins can be targeted for therapeutic or diagnostic purposes. A ztryp1 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylaianine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in *Xenopus oocytes* by microinjection of mutated mRNA and chemically aminoacylated suppressor tRNAs (Turcatti et al. *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amirio acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for ztryp1 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science*

255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related polypeptides such as human (α-tryptase and β-tryptase.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, *Current Opin. Struct. Biol.* 5:372–376, 1995 and Cordes et al., *Current Opin. Struct. Biol.* 6:3–10, 1996). In general, when designing modifications to molecules or identifying specific fragments determination of structure will be accompanied by evaluating activity of modified molecules.

Amino acid sequence changes are made in ztryp1 polypeptides so as to minimize disruption of higher order structure essential to biological activity. For example, when the ztryp1 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266–268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). It is generally believed that if a modified molecule does not have the same disulfide bonding pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205–214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961–964, 1992).

A HoppWoods hydrophilicity profile of the ztryp1 protein sequence as shown in SEQ ID NO:2 or SEQ ID NO:15 can be generated (Hopp et al., *Proc. Natl. Acad. Sci.* 78:3824–3828, 1981; Hopp, *J. Immun. Meth.* 88:1–18, 1986 and Triquier et al., *Protein Engineering* 11:153–169, 1998). The profile is based on a sliding six-residue window. Buried G, S, and T residues and exposed H, Y, and W residues were ignored. For example, in mouse ztryp1, hydrophilic regions include: (1) amino acid number 125 (Asn) to amino acid number 130 (Asp) of SEQ ID NO:2; (2) amino acid number 172 (Glu) to amino acid number 177 (His) of SEQ ID NO:2; (3) amino acid number 256 (Asp) to amino acid number 261 (Gln) of SEQ ID NO:2; (4) amino acid number 277 (Lys) to amino acid number 282 (Asp) of SEQ ID NO:2. In human ztryp1, corresponding hydrophilic regions include: (1) amino acid number 117 (Gln) to amino acid number 122 (Ser) of SEQ ID NO:15; (2) amino acid number 57 (Arg) to amino acid number 62 (Lys) of SEQ ID NO:15; (3) amino acid number 116 (His) to amino acid number 121 (Asn) of SEQ ID NO:15; (4) amino acid number 147 (Lys) to amino acid number 152 (Ser) of SEQ ID NO:15.

Those skilled in the art will recognize that hydrophilicity or hydrophobicity will be taken into account when designing modifications in the amino acid sequence of a ztryp1 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such as shown in SEQ ID NO:2 or SEQ ID NO:15. Cysteine residues of SEQ ID NO:2 OR SEQ ID NO: 15, will be relatively intolerant of substitution.

The identities of essential amino acids can also be inferred from analysis of sequence similarity between other tryptase family members with ztryp1. Using methods such as "FASTA" analysis described previously, regions of high similarity are identified within a family of proteins and used to analyze amino acid sequence for conserved regions. An alternative approach to identifying a variant ztryp1 polynucleotide on the basis of structure is to determine whether a nucleic acid molecule encoding a potential variant ztryp1 polynucleotide can hybridize to a nucleic acid molecule having the nucleotide sequence of SEQ ID NO:1 or SEQ ID NO:14, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl Acad. Sci. USA* 88:4498 (1991), Coombs and Corey, "Site-Directed Mutagenesis and Protein Engineering," in *Proteins: Analysis and Design*, Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. Site-directed mutagenesis and screening is routine for the skilled artisan. See also, Hilton et al., *J. Biol. Chem.* 271:4699 (1996).

The present invention also includes functional fragments of ztryp1 polypeptides and nucleic acid molecules encoding such functional fragments. A "functional" ztryp1 or fragment thereof defined herein is characterized by its proliferative or differentiating activity, by its ability to induce or inhibit specialized cell functions, or by its ability to bind specifically to an anti-ztryp1 antibody or ztryp1 receptor or binding partner (either soluble or immobilized). As previously described herein, ztryp1 is characterized by a serine protease and tryptase-like structure as shown in SEQ ID NO:2 or SEQ ID NO:15. Thus, the present- invention further provides fusion proteins encompassing: (a) polypeptide molecules comprising one or more of the domains, motifs, or residues described herein; and (b) functional fragments comprising one or more of these domains, motifs, or residues. The other polypeptide portion of the fusion protein may be contributed by another tryptase family member, such as human tryptase, trypsin, or the like or by a non-native and/or an unrelated secretory signal peptide that facilitates secretion of the fusion protein.

Routine deletion analyses of nucleic acid molecules can be performed to obtain functional fragments of a nucleic acid molecule that encodes a ztryp1 polypeptide. As an illustration, DNA molecules having the nucleotide sequence of SEQ ID NO:1 or SEQ ID NO:14 or fragments thereof, can be digested with Bal31 nuclease to obtain a series of nested deletions. These DNA fragments are then inserted into expression vectors in proper reading frame, and the expressed polypeptides are isolated and tested for ztryp1 activity, or for the ability to bind anti-ztryp1 antibodies or ztryp1 receptor. One alternative to exonuclease digestion is to use oligonucleotide-directed mutagenesis to introduce deletions or stop codons to specify production of a desired ztryp1 fragment. Alternatively, particular fragments of a ztryp1 polynucleotide can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther*. 66:507 (1995). Moreover, standard techniques for functional analysis of proteins are described by, for example, Treuter et al., *Molec. Gen. Genet*. 240:113 (1993); Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987); Herschman, "The EGF Receptor," in *Control of Animal Cell Proliferation* 1, Boynton et al., (eds.) pages 169–199 (Academic Press 1985); Coumailleau et al., *J. Biol. Chem*. 270:29270 (1995); Fukunaga et al., *J. Biol. Chem*. 270:25291 (1995); Yamaguchi et al., *Biochem. Pharmacol*. 50:1295 (1995); and Meisel et al., *Plant Molec. Biol*. 30:1 (1996).

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem*. 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed ztryp1 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., those with protease activity, that induce signal transduction or bind anti-tryp1 antibodies, and the like) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 or SEQ ID NO:15 or that retain, for example, tryptase-like properties, protease activity, mitogenic activity, induce cytokine secretion, binding, cell-cell communication, or signal transduction activity of the wild-type ztryp1 protein. For example, using the methods described herein, one could identify a receptor binding domain on ztryp1; heterodimeric and homodimeric binding domains; enzymatically active domains; other functional or structural domains; or other domains important for protein-protein interactions or signal transduction. Such polypeptides may also include additional polypeptide segments, such as affinity tags, as generally disclosed herein.

For any ztryp1 polypeptide, including variants and fusion proteins, one of ordinary skill in the art can readily generate a fully degenerate polynucleotide sequence encoding that variant using the information-set forth in Tables 1 and 2 above.

The ztryp1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., N.Y., 1987.

In general, a DNA sequence encoding a ztryp1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a ztryp1 polypeptide into the secretory pathway of a host cell, a secretory signal sequence (also known as a leader sequence, prepro sequence or pre sequence) is provided in the expression vector. The secretory signal sequence may be that of ztryp1, or may be derived from another secreted protein (e.g., t-PA) or synthesized de novo. The secretory signal sequence is operably linked to the ztryp1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from residue 1 (Met) to residue 23 (Ser) of SEQ ID NO:2, or from residue 1 (Met) to residue 18 (Ala) of SEQ ID NO:15 is operably linked to a DNA sequence encoding another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., Focus 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as “transfectants”. Cells that have been cultured in the presence of the selective agent and are able to pass the gene of interest to their progeny are referred to as “stable transfectants.” A preferred selectable marker is a gene encoding resistance to the antibiotic neomycin. Selection is carried out in the presence of a neomycin-type drug, such as G418 or the like. Selection systems can also be used to increase the expression level of the gene of interest, a process referred to as “amplification.” Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g,. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS soffing or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (*Banalore*) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculoviruis, commonly derived from *Autographa californica nuclear polyhedrosis virus* (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. The second method of making recombinant baculovirus utilizes a transposon-based system described by Luckow (Luckow, V. A, et al., *J Virol* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the ztryp1 polypeptide into a baculovirus genome maintained in *E. coli* as a large plasmid called a “bacmid.” The pFastBac1™ transfer vector utilizes the AcNPV polyhedrin promoter to drive the expression of the gene of interest, in this case ztryp1. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B.C. et al., *J. Gen. Virol.* 75:1551–6, 1994; and, Chazenbalk, G. D., and Rapoport, B., *J. Biol. Chem.* 270:1543–9, 1995. In such transfer vector constructs, a short or long version of the basic protein promoter can be used. Moreover, transfer vectors can be constructed which replace the native ztryp1 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native ztryp1 secretory signal sequence. In addition, transfer vectors can include an in-frame fusion with DNA encoding an epitope tag at the C- or N-terminus of the expressed ztryp1 polypeptide, for example, a Glu-Glu epitope tag (Grussenmeyer, T. et al., *Proc. Natl. Acad. Sci.* 82:7952–4, 1985). Using a technique known in the art, a transfer vector containing ztryp1 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses ztryp1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the T. ni cells. The cells are grown up from an inoculation density of approximately $2–5\times10^5$ cells to a density of $1–2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the ztryp1 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POTl vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and U.S. Pat. No. 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a ztryp1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to ≦80% purity, more preferably to ≦90% purity, even more preferably ≦95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant ztryp1 polypeptides (or chimeric ztryp1 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural or biochemical properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification. Moreover purification methods used to purify of human tryptase polypeptides can be used to purify ztryp1 polypeptides (see, Chan, H. et al., ibid.).

Moreover, using methods described in the art, polypeptide fusions, or hybrid ztryp1 proteins, are constructed using regions or domains of the inventive ztryp1 in combination with those of other tryptase family proteins (e.g. human α-tryptase and β-tryptase, or mouse ztryp1), or heterologous proteins (Sambrook et al., ibid., Altschul et al., ibid., Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between ztryp 1 of the present invention with the functionally equivalent domain(s) from another family member, such as human α-tryptase, β-tryptase, mouse ztryp1 or trypsin. Such domains include, but are not limited to, the secretory signal sequence, pre-pro peptide, conserved motifs and active site amino acids, binding pocket, active polypeptide, and transmembrane domain. Such fusion proteins would be expected to have a biological functional profile that is the same or similar to polypeptides of the present invention or other known tryptase family proteins, depending on the fusion constructed. Moreover, such fusion proteins may exhibit other properties as disclosed herein.

Standard molecular biological and cloning techniques can be used to swap the equivalent domains between the ztryp1 polypeptide and those polypeptides to which they are fused. Generally, a DNA segment that encodes a domain of interest, e.g., a ztryp1 active polypeptide or motif described herein, is operably linked in frame to at least one other DNA segment encoding an additional polypeptide and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a pro-polypeptide (or pro-protein); or a DNA construct would encode from N-terminus to C-terminus a fusion protein comprising a signal polypeptide followed by a pro-peptide, active polypeptide and C-terminal region; or as interchanged with equivalent regions from another protein. In a fusion polypeptide preferred embodiment, a DNA construct would encode a mature form of ztryp1 comprising amino acids operably linked in frame comprising amino acids 43 (Val) through 168 (Gly) of SEQ ID NO:15 followed by amino acids 171 (Leu) to 232 (Thr) of SEQ ID NO:2 followed by 231 (Ser) to 275 (Arg) of SEQ ID NO:15, as shown in SEQ ID NO:24. Within another preferred embodiment, the binding pocket of SEQ ID NO:24 comprises the mouse ztryp1 binding pocket, as described herein. Such fusion proteins can be expressed, isolated, and assayed for activity as described herein.

Ztryp1 polypeptides or fragments thereof may also be prepared through chemical synthesis. ztryp1 polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem.* 34:595, 1970. After the entire synthesis of the desired peptide on a solid support, the peptide-resin is with a reagent which cleaves the polypeptide from the resin and removes most of the side-chain protecting;groups. Such methods are well established in the art.

The activity of molecules of the present invention can be measured using a variety of assays that measure cleavage of a substrate indicator molecule, synthetic substrate, or substrate polypeptide. Such assays are well known in the art. For a general reference, see Chan, H. et al., *Prot. Express. Purif.* 15:251–257, 1999; and Cromlish, J. A. et al., *J. Biol. Chem.* 262:1363–1373, 1987. Specific assays include, but are not limited to bioassays measuring fluorescence due to hydrolysis of 4-methylumbelliferone, hydrolysis of a substrate such as Tosyl-Gly-Pro-Lys-pNA (where "tosyl" is a 4-toluenesulfonyl and "pNA" is a p-nitroaniline moiety) and detection of UV, fibrinogen cleavage, and inhibition studies using various general and specific protease inhibitors which are routine in the art.

Proteins of the present invention are useful for inducing cell proliferation, inflammatory response, and cytokine production and in treating reproductive, testicular, heart, and other disorders. For example IL-8 production, inflammatory response or cell proliferation can be measured in vitro using cultured cells or in vivo by administering molecules of the claimed invention to the appropriate animal model. For instance, host cells expressing a secreted form of ztryp1 polypeptide may be embedded in an alginate environment and injected (implanted) into recipient animals. Alginate-poly-L-lysine microencapsulation, permselective membrane encapsulation and diffusion chambers are a means to entrap transfected mammalian cells or primary mammalian cells to permit the diffusion of proteins and other macromolecules secreted or released by the captured cells to the recipient animal. Most importantly, the capsules mask and shield the foreign, embedded cells from the recipient animal's immune response. Such encapsulations can extend the life of the injected cells from a few hours or days (naked cells) to several weeks (embedded cells). Alginate threads provide a simple and quick means for. generating embedded cells and testing, in vivo, the proteins secreted therefrom.

The materials needed to generate the alginate threads are known in the art. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of about 15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle). A large bore needle is then attached to the syringe, and the thread is intraperitoneally injected into a recipient in a minimal volume of Lactated Ringer's Solution.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an El gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S.E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

Ztryp1 is highly expressed in a tissue that contracts, and may affect other contractile tissues. Like human tryptase, ztryp1 may affect contractile tissues such as lung, gastrointestinal and heart tissues. For example contractile tissues in which ztryp1 is expressed include tissues in testis, e.g., vas deferens; prostate tissues; others where ztryp1 may be expressed or active include gastrointestinal tissues, e.g., colon and small intestine; and heart. The effects of ztryp1 polypeptide, its antagonists and agonists, on tissue contractility can be measured in vitro using a tensiometer with or without electrical field stimulation. Such assays are known in the art and can be applied to tissue samples, such as aortic rings, vas deferens, ilium, uterine and other contractile tissue samples, as well as to organ systems, such as atria, and can be used to determine whether ztryp1 polypeptide, its agonists or antagonists, enhance or depress contractility. Molecules of the present invention are hence useful for treating dysfunction associated with contractile tissues or can be used to suppress or enhance contractility in vivo. As such, molecules of the present invention have utility in treating cardiovascular disease, infertility, in vitro fertilization, birth control, treating impotence or other male reproductive dysfunction, as well as inducing birth.

The effect of the ztryp1 polypeptides, antagonists and agonists of the present invention on contractility of tissues including uterus, prostate, testis, gastrointestinal tissues, and heart can be measured in a tensiometer that measures contractility and relaxation in tissues. See, Dainty et al., *J. Pharmacol.* 100:767, 1990; Rhee et al., *Neurotox.* 16: 179, 1995; Anderson, M. B., *Endocrinol.* 114:364–368, 1984; and Downing, S. J. and Sherwood, O. D, *Endocrinol.* 116:1206–1214, 1985. For example, measuring vasodilatation of aortic rings is well known in the art. Briefly, aortic rings are taken from 4 month old Sprague Dawley rats and placed in a buffer solution, such as modified Krebs solution (118.5 mM NaCl, 4.6 mM KCl, 1.2 mM $MgSO_4.7H_2O$, 1.2 mM $KH_2PO_4$, 2.5 mM $CaCl_2.2H_2O$, 24.8 mM $NaHCO_3$ and 10 mM glucose). One of skill in the art would recognize that this method can be used with other animals, such as rabbits, other rat strains, Guinea pigs, and the like. The rings are then attached to an isometric force transducer (Radnoti Inc., Monrovia, Calif.) and the data recorded with a Ponemah physiology platform (Gould Instrument systems, Inc., Valley View, Ohio) and placed in an oxygenated (95% $O_2$, 5% $CO_2$) tissue bath containing the buffer solution. The tissues are adjusted to 1 gram resting tension and allowed to stabilize for about one hour before testing. The integrity of the rings can be tested with norepinepherin (Sigma Co., St. Louis, Mo.) and Carbachol, a muscarinic acetylcholine agonist (Sigma Co.). After integrity is checked, the rings are washed three times with fresh buffer and allowed to rest for about one hour. To test a sample for vasodilatation, or relaxation of the aortic ring tissue, the rings are contracted to two grams tension and allowed to stabilize for fifteen minutes. A ztryp1 polypeptide sample is then added to 1, 2 or 3 of the 4 baths, without flushing, and tension on the rings recorded and compared to the control rings containing buffer only. Enhancement or relaxation of contractility by ztryp1 polypeptides, their agonists and antagonists is directly measured by this method, and it can be applied to other contractile tissues such as uterus, prostate, gastrointestinal tissues and testis.

Gastric motility is generally measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. A test food or liquid is radiolabeled with an isotope (e.g. $^{99m}$Tc), and after ingestion or administration, transit time through the gastrointestinal tract and gastric emptying are measured by visualization using gamma cameras (Meyeret al., *Am. J. Dig. Dis.* 21:296, 1976; Collins et al., *Gut* 24:1117, 1983; Maughan et al., *Diabet. Med.* 13 9 Supp. 5:S6–10, 1996 and Horowitz et al., *Arch. Intern. Med.* 145:1467–1472, 1985). These studies may be performed before and after the administration of a promotility agent to quantify the efficacy of the drug.

As a secreted molecule, the activity of ztryp1 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharnacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including ztryp1 polypeptide, its agonists, or antagonists. Preferably, the microphysiometer is used to measure responses of a ztryp1-responsive eukaryotic cell, compared to a control eukaryotic cell that does not respond to ztryp1 polypeptide. Ztryp1-responsive eukaryotic cells comprise cells into which a receptor for ztryp1 has been transfected creating a cell that is responsive to ztryp1; or cells naturally responsive to ztryp1 such as cells derived from testicular tissue. Differences, measured by a change, for example, an increase or diminution in extracellular acidification, in the response of cells exposed to ztryp1 polypeptide, relative to a control not exposed to ztryp1, are a direct measurement of ztryp1-modulated cellular responses. Moreover, such ztryp1-modulated responses can be assayed under a variety of stimuli. Using the microphysiometer, there is provided a method of identifying agonists of ztryp1 polypeptide, comprising providing cells responsive to a ztryp1 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Moreover, culturing a third portion of the cells in the presence of ztryp1 polypeptide and the absence of a test compound can be used as a positive control for the ztryp1-responsive cells, and as a control to compare the agonist activity of a test compound with that of the ztryp1 polypeptide. Moreover, using the microphysiometer, there is provided a method of identifying antagonists of ztryp1 polypeptide, comprising providing cells responsive to a ztryp1 polypeptide, culturing a first portion of the cells in the presence of ztryp1 and the absence of a test compound, culturing a second portion of the cells in the presence of ztryp1 and the presence of a test compound, and detecting a change, for example, an increase or a diminution in a cellular response of the second portion of the cells as compared to the first portion of the cells. The change in cellular response is shown as a measurable change extracellular acidification rate. Antagonists and agonists, for ztryp1 polypeptide, can be rapidly identified using this method.

Moreover, ztryp1 can be used to identify cells, tissues, or cell lines which respond to a ztryp1-stimulated pathway. The microphysiometer, described above, can be used to rapidly identify ligand-responsive cells, such as cells responsive to ztryp1 of the present invention. Cells can be cultured in the presence or absence of ztryp1 polypeptide. Those cells which elicit a measurable change in extracellular acidification in the presence of ztryp1 are responsive to ztryp1. Such cell lines, can be used to identify antagonists and agonists of ztryp1 polypeptide as described above.

Ztryp1 polypeptide can be used to identify inhibitors (antagonists) of its activity. Test compounds are added to the biological or biochemical assays disclosed herein to identify compounds that inhibit the activity of ztryp1. In addition to those assays disclosed herein, samples can be tested for inhibition of ztryp1 activity within a variety of assays designed to measure receptor binding or the stimulation/inhibition of ztryp1-dependent cellular responses. For example, ztryp1-responsive cell lines can be transfected with a reporter gene construct that is responsive to a ztryp1-stimulated cellular pathway. Reporter gene constructs of this type are known in the art, and will generally comprise a ztryp1-DNA response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Moreover, the tryptase-like ztryp1 of the present invention could interact with cellular receptors analogous to human trypsin which has been shown to activate both the thrombin receptor and PAR-2 (See, Molino, M. et al., *J. Biol. Chem.* 272:4043–4049, 1997). The methods disclosed in Molino et al., can be used to assess whether ztryp1 interacts with thrombin receptor, PAR-2 or related receptors. Candidate compounds that serve as test samples including solutions, mixtures or extracts, are tested for the level of response to the ztryp1 polypeptide. The ability of a test sample to inhibit the activity of ztryp1 polypeptide on the target cells as evidenced by a decrease in ztryp1 stimulation of reporter gene expression in the presence of a test sample relative to a control which was cultured in the absence of a test sample. Assays of this type will detect compounds that directly block ztryp1 binding to cell-surface receptors, e.g., dimerization, as well as compounds that block processes in the cellular pathway subsequent to receptor-ligand binding. Alternatively, compounds or other samples can be tested for direct blocking of ztryp1 binding to receptor using ztryp1 tagged with a detectable label (e.g., $^{125}I$, biotin, horseradish peroxidase, FITC, and the like). Within assays of this type, the ability of a test sample to inhibit the binding of labeled ztryp1 to the receptor is indicative of inhibitory activity, which can be confirmed through secondary assays. Receptors used within binding assays may be cellular receptors or isolated, immobilized receptors.

Antagonists are also useful as research reagents for characterizing sites of ligand-receptor interaction. Inhibitors of ztryp1 activity (ztryp1 antagonists) include anti-ztryp1 antibodies and soluble proteins which bind ztryp1 polypeptide, as well as other peptidic and non-peptidic agents (including ribozymes).

Alternatively, the above methodology may be used to identify agonists of ztryp1 activity. Candidate compounds serving as test samples including solutions, mixtures or extracts, are tested for the ability to mimic the activity of ztryp1 polypeptide on the target cells as evidenced by stimulation of reporter gene expression in the presence of a test sample and the absence of ztryp1, relative to a control (cultured in the absence of a test sample and the absence of ztryp1 polypeptide), using assays as described above. Mouse or human ztryp1 agonists and antagonists may act on the counterpart human ortholog of ztryp1 or in other animal species.

In view of the tissue distribution observed for ztryp1, agonists (including the natural ligand/substrate/cofactor/etc.) and antagonists have enormous potential in both in vitro and in vivo applications. Compounds identified as ztryp1 agonists are useful for stimulating cell growth or signal transduction in vitro and in vivo. Agonists and ztryp1 are thus useful in specifically promoting the growth and/or development of cells in culture. Considering the high expression of ztryp1 in testis, ztryp1 polypeptides and ztryp1 agonists may be particularly useful as research reagents, particularly for the growth of testicular types, animal eggs, construction of transgenic or knockout mice, cells from animal embryos or primary cultures derived from these tissues, and in animal breeding applications. As such, ztryp1 polypeptide can be provided as a supplement in cell culture medium.

Moreover, as a protease, both mouse and human ztryp1 serve as a useful research tool in molecular biology and biochemical applications. For example, ztryp1 cleavage can be used to characterize and identify proteins and protein families by the cleavage patterns generated upon exposure to ztryp1. Such cleavage patterns or "cleavage maps" are useful in the art in characterizing proteins generally, as they can be used to identify proteins, and characterize their structure, as well as serve as an educational tool to aid in the characterization of proteins; such uses for ztryp1 are similar to proteases known in the art, such as trypsin, chymo-trypsin and the like (See, for example, Ausubel et al., (eds.), *Current Protocols in Molecular Biology* John Wiley and Sons, Inc. 1987)). Moreover, ztryp1 can be used to activate proteins that require ztryp1 cleavage. Moreover, similar to other known proteases, ztryp1 can be used in preparations of DNA and RNA, and the like, that require inactivation of proteins, DNAses, RNAses, and the like. A protease, such as ztryp1 serves as a useful reagent to dissociate adherent cells from tissue culture plates. Such applications for the novel ztryp1 protease are well known by one of skill in the art. See, for example, Sambrook et al., *Molecular Cloning: A Laboratory Manual*, Second Edition (Cold Spring Harbor Press 1989); Ausubel et al., (eds.), supra.; Berger and Kimmel (eds.), *Guide to Molecular Cloning Techniques*, (Academic Press, Inc. 1987); and Wetmur, *Crit. Rev. Biochem. Mol. Biol.* 26:227 (1990)). Moreover, ztryp1 can have further industrial applicability in industries that utilize proteases, for example, as a detergent enzyme, food processing enzyme, and the like. Such applications for the novel ztryp1 protease are well known by one of skill in the art.

The tissue specificity of ztryp1 expression suggests a role in spermatogenesis, a process that is remarkably similar to the development of blood cells (hematopoiesis). Briefly, spermatogonia undergo a maturation process similar to the differentiation of hematopoietic stem cells. In view of the tissue specificity observed for ztryp1, agonists and antagonists have enormous potential in both in vitro and in vivo applications. Ztryp1 polypeptides, agonists and antagonists may also prove useful in modulating spermatogenesis and thus aid in overcoming infertility. Antagonists are useful as research reagents for characterizing sites of ligand-receptor interaction. In vivo, ztryp1 polypeptides, agonists or antagonists may find application in the treatment of male infertility or as a male contraceptive agent, or in animal breeding.

The ztryp1 polypeptides, antagonists of agonists, of the present invention can also modulate sperm capacitation. Before reaching the oocyte or egg and initiating an egg-sperm interaction, the sperm must be activated. The sperm undergo a gradual capacitation, lasting up to 3 or 4 hours in vitro, during which the plasma membrane of the sperm head and the outer acrosomal membrane fuse to form vesicles that facilitate the release of acrosomal enzymes. The acrosomal membrane surrounds the acrosome or acrosomal cap which is located at the anterior end of the nucleus in the sperm head. In order for the sperm to fertilize egg the sperm must penetrate the oocyte. To enable this process the sperm must undergo acrosomal exocytosis, also known as the acrosomal reaction, and release the acrosomal enzymes in the vicinity of the oocyte. These enzymes enable the sperm to penetrate the various oocyte layers, (the cumulus oophorus, the corona radiata and the zona pellucida). The released acrosomal enzymes include hyaluronidase and proacrosin, in addition to other enzymes such as proteases. During the acrosomal reaction, proacrosin is converted to acrosin, the active form of the enzyme, which is required for and must occur before binding and penetration of the zona pellucida is possible. A combination of the acrosomal lytic enzymes and sperm tail movements allow the sperm to penetrate the oocyte layers. Numerous sperm must reach the egg and release acrosomal enzymes before the egg can finally be fertilized. Only one sperm will successfully bind to, penetrate and fertilize the egg, after which the zona hardens so that no other sperm can penetrate the egg (Zaneveld, in *Male Infertility*, Chapter 11, Comhaire (Ed.), Chapman & Hall, London, 1996). Peptide hormones, such as insulin homologs are associated with sperm activation and egg-sperm interaction. For instance, capacitated sperm incubated with relaxin show an increased percentage of progressively motile sperm, increased zona penetration rates, and increased percentage of viable acrosome-reacted sperm (Carrell et al., *Endocr. Res.* 21:697–707, 1995). As ztryp1 has structural similarity to proteases and has protease activity, it may cleave or process hormones and other proteases such as peptide prohormones, and the like to their active forms. Moreover, tissue-specific localization of Ztryp1 to the testis, suggests that the ztryp1 polypeptides described herein play a role in the function or reproductive processes in this tissue.

Accordingly, proteins of the present invention can have applications in enhancing fertilization during assisted reproduction in humans and in animals. Such assisted reproduction methods are known in the art and include artificial insemination, in vitro fertilization, embryo transfer and gamete intrafallopian transfer. Such methods are useful for assisting men and women who have physiological or metabolic disorders preventing natural conception or can be used to enhance in vitro fertilization. Such methods are also used in animal breeding programs, such as for livestock breeding and can be used as methods for the creation of transgenic animals. Proteins of the present invention can be combined with sperm, an egg or an egg-sperm mixture prior to fertilization of the egg. In some species, sperm capacitate spontaneously during in vitro fertilization procedures, but normally sperm capacitate over an extended period of time both in vivo and in vitro. It is advantageous to increase sperm activation during such procedures to enhance the likelihood of successful fertilization. The washed sperm or sperm removed from the seminal plasma used in such assisted reproduction methods has been shown to have altered reproductive functions, in particular, reduced motility and zona interaction. To enhance fertilization during assisted reproduction methods sperm is capacitated using exogenously added compounds. Suspension of the sperm in seminal plasma from normal subjects or in a "capacitation media" containing a cocktail of compounds known to activate sperm, such as caffeine, dibutyl cyclic adenosine monophosphate (dbcAMP) or theophylline, have resulted in improved reproductive function of the sperm, in particular, sperm motility and zonae penetration (Park et al., *Am. J. Obstet. Gynecol.* 158:974–9, 1988; Vandevoort et al., Mol. Repro. Develop. 7:299–304, 1993; Vandevoort and Overstreet, *J. Androl.* 16:327–33, 1995). The presence of immunoreactive relaxin in vivo and in association with cryopreserved semen, was shown to significantly increase sperm motility (Juang et al., *Anim. Reprod. Sci.* 20:21–9, 1989; Juang et al., *Anim. Reprod. Sci.* 22:47–53, 1990). Porcine relaxin stimulated sperm motility in cryopreserved human sperm (Colon et al., *Fertil. Steril.* 46:1133–39, 1986; Lessing et al., *Fertil. Steril.* 44:406–9, 1985) and preserved ability of washed human sperm to penetrate cervical mucus in vitro (Brenner et al., *Fertil. Steril.* 42:92–6, 1984). Polypeptides of the present invention can used in such methods to enhance viability of cryopreserved sperm, enhance sperm motility and enhance fertilization, particularly in association with methods of assisted reproduction.

In cases where pregnancy is not desired, ztryp1 polypeptide or polypeptide fragments may function as germ-cell-specific antigens for use as components in "immunocontraceptive" or "anti-fertility" vaccines to induce formation of antibodies and/or cell mediated immunity to selectively inhibit a process, or processes, critical to successful reproduction in humans and animals. The use of sperm and testis antigens in the development of immunocontraceptives have been described (O'Hern et al., *Biol Reprod.* 52:311–39, 1995; Diekman and Herr, *Am. J. Reprod. Immunol.* 37:111–17, 1997; Zhu and Naz, *Proc. Natl. Acad. Sci. USA* 94:4704–9,1997). A vaccine based on human chorionic gonadotrophin (HCG) linked to a diphtheria or tetanus carrier was in clinical trials (Talwar et al., *Proc. Natl. Acad. Sci. USA* 91:8532–36, 1994). A single injection resulted in production of high titer antibodies that persisted for nearly a year in rabbits (Stevens, *Am. J. Reprod. Immunol.* 29:176–88, 1993). Such methods of immunocontraception using vaccines would include a ztryp1 testes-specific protein or fragment thereof. The Ztryp1 protein or fragments can be conjugated to a carrier protein or peptide, such as tetanus or diphtheria toxoid. An adjuvant, as described above, can be included and the protein or fragment can be non-covalently associated with other molecules to enhance intrinsic immunoreactivity. Methods for administration and methods for determining the number of administrations are known in the art. Such a method might include a number of primary injections over several weeks followed by booster injections as needed to maintain a suitable antibody titer. Moreover, the anti-ztryp1 antibodies of the present invention can also be used as immunocontraceptives.

Moreover, mouse ztryp1 transgenic and knockout mice and mice can be used as a fertility or contraception animal model, and can be used to test the effects of test compounds that influence ztryp1 activity on fertility.

The polypeptides, nucleic acid and/or antibodies of the present invention can be used as a model to study or be applied in treatment of disorders associated with asthma, the immune system, gastrointestinal system, heart, inflammation, lymph system, and testis. The polypeptides, agonists, antagonists, nucleic acid and/or antibodies of the present invention can be used in treatment of disorders associated with asthma, vascular function such as stroke, inflammation and testicular function. The molecules of the present invention may used to modulate or to treat or prevent development of pathological conditions. In particular, certain syndromes or diseases can be amenable to such diagnosis, treatment or prevention.

In addition, polypeptides of the present invention can be used for their ability to modify inflammation. Methods to assess proinflammatory or antiinflammatory qualities of ztryp1 are known in the art. For example, suppression of cAMP production is an indication of anti-inflammatory effects (Nihei, Y., et al., *Arch. Dermatol. Res.*, 287:546–552, 1995). Ztryp1, likewise can exhibit similar anti-inflammatory effects, and may exert these effects in tissues in which it is expressed. For example, ztryp1 is expressed in testis and can be useful in treatment of inflammation in this tissue. Moreover, ztryp1 may be expressed in the small intestine, and can be useful in treatment of inflammatory bowel disease, diverticulitis, inflammation during and after intestinal surgery, and the like. In addition, ztryp1, if expressed in PBLs and bone marrow, can have other anti-inflammatory actions in heart, pelvic inflammatory disease, (PID), psoriasis, arthritis, and other inflammatory diseases. Moreover, mouse ztryp1 transgenic and knockout mice and mice can be used as an animal model for inflammation, and can be used to test the effects of test compounds, agonists and antagonists that influence ztryp1 activity on inflammation.

As such, ztryp1 polypeptide, or its agonists or antagonists, have potential uses in inflammatory diseases such as asthma and arthritis. For example, ztryp1, like known tryptases, can be inflammatory; thus, antagonists would be valuable in asthma therapy or other anti-inflammatory therapies where migration of lymphocytes is damaging. Alternatively, ztryp1 can have an inhibitory or competitive effect on inflammatory agents and may serve directly as an asthma therapeutic or anti-inflammatory. In addition, ztryp1 can serve other important roles in lung function, for instance, bronchodilation or broncoconstriction, tissue elasticity, recruitment of lymphocytes in lung infection and damage. Assays to-assess the activity of ztryp1 in lung cells are discussed in Laberge, S. et al., *Am. J. Respir. Cell Mol. Biol.* 17:193–202, 1997; Rumsaeng, V. et al., *J. Immunol.*, 159:2904–2910, 1997; and Schluesener, H. J. et al., *J. Neurosci. Res.* 44:606–611, 1996. Methods to determine proinflammatory and antinflammatory qualities of ztryp1 or its antagonists are known in the art. Moreover, other molecular biological, immunological, and biochemical techniques known in the art and disclosed herein can be used to determine ztryp1 activity and to isolate agonists and antagonists. Moreover, mouse ztryp1 transgenic and knockout mice and mice can be used as an asthma model, and can be used to test the effects of test compounds that influence ztryp1 activity on asthma or lung function.

Both ztryp1 modulated direct and indirect inflammation can be assayed by methods in the art. For example see, Hamada, T. et al. *J. Exp. Med.* 188:539–548, 1998; and Liu, L. et al., *J. Immunol.* 161:3064–3070, 1998. For example, proinflammatory effects of ztryp1 polypeptide can be directly tested in assays using a Transwell™ (Costar), wherein endothelial cells are plated on a semi-permeable membrane and ztryp1 polypeptide is present in the lower chamber of the transwell and $Cr^{51}$ or fluorescently-labeled neutrophils (PMNs), lymphocytes, HL60 cells, K562 cells, or the like are added on to the upper chamber of the transwell. Migration of the PMNs and the like to the lower chamber of the transwell in the presence of ztryp1 polypeptide, but not its absence (Negative control), would demonstrate ztryp1 polypeptide as a direct chemoattractant of the PMNs. Moreover, IL-8 could be employed in this assay as a positive control. To test ztryp1 as indirect stimulator of inflammatory response, a similar method can be employed. For example, an experiment can be set up as per above where in addition to the presence of ztryp1 on the lower chamber of the transwell, fibroblast or adipocytes are plated there. In this way, effects of ztryp1 polypeptide in inducing these cells to secrete factors that enhance migration of PMNs, i.e., inflammation, can be measured. The bFGF can be. used as a positive control for indirect assay. Anti-inflammatory effects of ztryp1 polypeptide can also be measured when added on the upper chamber in the presence of PMN's using a similar transwell assay known in the art.

A ztryp1 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify complementary polypeptides, as an in vitro assay tool, or zrtyp1 antagonist. For use in assays, the chimeras are bound to a support via the $F_c$ region and used in an ELISA format.

A ztryp1 receptor-binding polypeptide can also be used for purification of receptor. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids, cell lysates or membrane fractions containing receptors are passed through the column one or more times to allow ligand to bind to the receptor polypeptide. The receptor is then eluted using changes in salt concentration, chaotropic agents (guanidine HCl), or pH to disrupt ligand-receptor binding.

Molecules of the present invention can be used to identify and isolate receptors involved in testicular function. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

Ztryp1 polypeptides can also be used to prepare antibodies that bind to ztryp1 epitopes, peptides or polypeptides. The ztryp1 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a ztryp1 polypeptide (e.g., SEQ ID NO:2 or SEQ ID NO: 15). Polypeptides comprising a larger portion of a ztryp1 polypeptide, i.e., from 30 to 10 residues up to the entire length of the amino acid sequence are included. Antigens or immunogenic epitopes can also include attached tags, adjuvants and carriers, as described herein. Suitable antigens include the ztryp1 polypeptide encoded by SEQ ID NO:2 from amino acid number 44 (Val) to amino acid number 276 (Ile) (i.e., the active polypeptide), or a contiguous 9 to 232 amino acid fragment thereof. Suitable antigens include the ztryp1 polypeptide encoded by SEQ ID NO:15 from amino acid number 43 (Val) to amino acid number 275 (Arg) (i.e., the mature active polypeptide), or a contiguous 9 to 233 amino acid fragment thereof. Other suitable antigens include the pre-pro peptide, binding pocket, hydrophilic domains, extracellular domains, motifs, domains, regions, epitopes, as disclosed herein. Preferred peptides to use as antigens are hydrophilic peptides such as those predicted by one of skill in the art from a hydrophobicity plot such as a Hopp/Woods hydrophilicity profile based on a sliding six-residue window, with buried G, S, and T residues and exposed H, Y, and W residues ignored. Such Ztryp1 hydrophilic peptides include peptides comprising amino acid sequences selected from the group consisting of: (1) amino acid number 125 (Asn) to amino acid number 130 (Asp) of SEQ ID NO:2; (2) amino acid number 172 (Glu) to amino acid number 177 (His) of SEQ ID NO:2; (3) amino acid number 256 (Asp) to amino acid number 261 (Gln) of SEQ ID NO:2; (4) amino acid number 277 (Lys) to amino acid number 282 (Asp) of SEQ ID NO:2; and (5) amino acid number 117 (Gln) to amino acid number 122 (Ser) of SEQ ID NO:15; (6) amino acid number 57 (Arg) to amino acid number 62 (Lys) of SEQ ID NO:15; (7) amino acid number 116 (His) to amino acid number 121 (Asn) of SEQ ID NO:15; (8) amino acid number 147 (Lys) to amino acid number 152 (Ser) of SEQ ID NO:15. Antigenic epitopes as predicted from a Jameson-Wolf plot of SEQ ID NO:2 or SEQ ID NO:15, for example, using a DNA*STAR program, are also included as antigens for use in generating anti-ztryp1 antibodies. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a ztryp1 polypeptide or a fragment thereof. The immunogenicity of a ztryp1 polypeptide may be increased through the use of an adjuvant, such as alum (aluminum hydroxide) or Freund's complete or incomplete adjuvant. Polypeptides useful for immunization also include fusion polypeptides, such as fusions of ztryp1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-ztryp1 antibodies herein bind to a ztryp1 polypeptide, peptide or epitope with an affinity at least 10-fold greater than the binding affinity to control (non-ztryp1) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Whether anti-ztryp1 antibodies do not significantly cross-react with related polypeptide molecules is shown, for example, by the antibody detecting ztryp1 polypeptide but not known related polypeptides using a standard Western blot analysis (Ausubel et al., ibid.). Examples of known related polypeptides are those disclosed in the prior art, such as known orthologs, and paralogs, and similar known members of a protein family (e.g., known human tryptases). Screening can also be done using known non- mouse or human ztryp1, and ztryp1 mutant polypeptides. Moreover, antibodies can be "screened against" known related polypeptides, to isolate a population that specifically binds to the ztryp1 polypeptides. For example, antibodies raised to ztryp1 are adsorbed to related polypeptides adhered to insoluble matrix; antibodies specific to ztryp1 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988*; Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988*; Monoclonal Antibodies: Principles and Practice*, Goding, J. W. (eds.), *Academic Press Ltd*., 1996; Benjamin et al., *Ann. Rev. Immunol.* 2: 67–101, 1984. Specifically binding anti-ztryp1 antibodies can be detected by a number of methods in the art, and disclosed below.

A variety of assays known to those skilled in the art can be utilized to detect antibodies which bind to ztryp1 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant ztryp1 protein or polypeptide.

Alternative techniques for generating or selecting antibodies useful herein include in vitro exposure of lymphocytes to: ztryp1 protein or peptide, and selection of antibody display libraries in phage or similar vectors (for instance, through use of immobilized or labeled ztryp1 protein or peptide). Genes encoding polypeptides having potential ztryp1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the ztryp1 sequences disclosed herein to identify proteins which bind to ztryp1. These "binding polypeptides" which interact with ztryp1 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of ztryp1 polypeptides; for detecting or quantitating soluble ztryp1 polypeptides as marker of underlying pathology or disease. These binding polypeptides can also act as ztryp1 "antagonists" to block ztryp1 binding and signal transduction in vitro and in vivo. These anti-ztryp1 binding polypeptides would be useful for inhibiting ztryp1 activity or protein-binding.

Antibodies to ztryp1 may be used for tagging cells that express ztryp1; for isolating ztryp1 by affinity purification; for diagnostic assays for determining circulating levels of ztryp1 polypeptides; for detecting or quantitating soluble ztryp1 as marker of underlying pathology or disease; in analytical methods employing FACS; for screening expression libraries; for generating anti-idiotypic antibodies; and as neutralizing antibodies or as antagonists to block ztryp1 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to ztryp1 or fragments thereof may be used in vitro to detect denatured ztryp1 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, ztryp1 polypeptides or anti-ztryp1 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, ztryp1-cytokine fusion proteins or antibody-cytokine fusion proteins can be used for enhancing in vivo killing of target tissues (for example, blood and bone marrow cancers), if the ztryp1 polypeptide or anti-ztryp1 antibody targets the hyperproliferative blood or bone marrow cell (See, generally, Homick et al., *Blood* 89:4437–47, 1997). They described fusion proteins enable targeting of a cytokine to a desired site of action, thereby providing an elevated local concentration of cytokine. Suitable ztryp1 polypeptides or anti-ztryp1 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the ztryp1 polypeptide or anti-ztryp1 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The novel polypeptides of the present invention may be useful for studies to isolate mesenchymal stem cells and myocyte or other progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, the present invention includes a polypeptide that may be indirectly involved (e.g., via processing a prohormone or other regulatory peptide to an active polypeptide) in stimulating or inhibiting the proliferation of lymphoid cells, hematopoietic cells, endothelial cells, testicular cells, or cancer cells. Thus polypeptide and antibody molecules of the present invention may have use in inhibiting tumor cells, and particularly testicular tumor cells.

Assays measuring differentiation include, for example, measuring cell markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference). Alternatively, ztryp1 polypeptide itself can serve as an additional cell-surface or secreted marker associated with stage-specific expression of a tissue. As such, direct measurement of ztryp1 polypeptide, or its loss of expression in a tissue as it differentiates, can serve as a marker for differentiation of tissues.

Similarly, direct measurement of ztryp1 polypeptide, or its loss of expression in a tissue can be determined in a tissue or cells as they undergo tumor progression. Increases in invasiveness and motility of cells, or the gain or loss of expression of ztryp1 in a pre-cancerous or cancerous condition, in comparison to normal tissue, can serve as a diagnostic for transformation, invasion and metastasis in tumor progression. For example, ztryp1 is highly expressed in testis, and appears to have very little expression in other tissues, therefore increased expression of ztryp1 in non-testis tissues can be indicative of transformation, cancer, or metastasis in the non-testicular tissue. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to ztryp1 expression. For example, appearance or disappearance of polypeptides that regulate cell motility can be used to aid diagnosis and prognosis of prostate cancer (Banyard, J. and Zetter, B. R., *Cancer and Metast. Rev.* 17:449–458, 1999). As a testis-specific molecule, ztryp1 gain or loss of expression of mRNA or polypeptide may serve as a diagnostic for testicular and other cancers.

In addition, as ztryp1 is testis-specific, polynucleotide probes, anti-ztryp1 antibodies, and detection the presence of ztryp1 polypeptides in tissue can be used to assess whether testicular tissue is present, for example, after surgery involving the excision of testis. As such, the polynucleotides, polypeptides, and antibodies of the present invention can be used as an aid to determine whether all testicular tissue is excised after surgery, for example, after surgery for testicular cancer. In such instances, it is especially important to remove all potentially diseased tissue to maximize recovery from the cancer, and to minimize recurrence. Preferred embodiments include fluorescent, radiolabeled, or calorimetrically labeled antibodies, that can be used in situ.

Moreover, the activity and effect of ztryp1 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly MS, et al. *Cell* 79: 315–328,1994). C57BL6/J mice are treated with an experimental agent either through daily injection of recombinant protein, agonist or antagonist or a one-time injection of recombinant adenovirus. Three days following this treatment, $10^5$ to $10^6$ cells are implanted under the dorsal skin. Alternatively, the cells themselves may be infected with recombinant adenovirus, such as one expressing ztryp1, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500–1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., ztryp1, on the ability of the tumor to recruit vasculature and undergo metastasis can thus be assessed. In addition, aside from using adenovirus, the implanted cells can be transiently transfected with ztryp1. Use of stable ztryp1 transfectants as well as use of induceable promoters to activate ztryp1 expression in vivo are known in the art and can be used in this system to assess ztryp1 induction of metastasis. Moreover, purified ztryp1 or ztryp1 conditioned media can be directly injected in to this mouse model, and hence be used in this system. For general reference see, O'Reilly MS, et al. *Cell* 79:315–328, 1994; and Rusciano D, et al. Murine Models of Liver Metastasis. *Invasion Metastasis* 14:349–361, 1995.

The activity of ztryp1 and its derivatives (conjugates) on growth and dissemination of tumor cells derived from human hematologic malignancies can also be measured in vivo in a mouse xenograft model. Several mouse models have been developed in which human tumor cells are implanted into immunodeficient mice, collectively referred to as xenograft models. See Cattan, A R and Douglas, *E Leuk. Res.* 18:513–22, 1994; and Flavell, D J, *Hematological Oncology* 14:67–82, 1996. The characteristics of the disease model vary with the type and quantity of cells delivered to the mouse. Typically, the tumor cells will proliferate rapidly and can be found circulating in the blood and populating numerous organ systems. Therapeutic strategies appropriate for testing in such a model include antibody induced toxicity, ligand-toxin conjugates or cell-based therapies. The latter method, commonly referred to adoptive immunotherapy, involves treatment of the animal with components of the human immune system (i.e. lymphocytes, NK cells) and may include ex vivo incubation of cells with ztryp1 or other immunomodulatory agents.

Polynucleotides encoding ztryp1 polypeptides are useful within gene therapy applications where it is desired to increase or inhibit ztryp1 activity. If a mammal has a mutated or absent ztryp1 gene, the ztryp1 gene can be introduced into the cells of the mammal. In one embodiment, a gene encoding a ztryp1 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a ztryp1 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95107358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit ztryp1 gene transcription, such as to inhibit cell proliferation in vivo. Polynucleotides that are complementary to a segment of a ztryp1-encoding polynucleotide (e.g., a polynucleotide as set forth in SEQ ID NO:1 or SEQ ID NO: 14) are designed to bind to ztryp1-encoding mRNA and to inhibit translation of such mRNA. Such antisense polynucleotides are used to inhibit expression of ztryp1 polypeptide-encoding genes in cell culture or in a subject.

The present invention also provides reagents which will find use in diagnostic applications. For example, the ztryp1 gene, a probe comprising ztryp1 DNA or RNA or a subsequence thereof can be used to determine if the ztryp1 gene is present on a chromosome or if a mutation has occurred. Detectable chromosomal aberrations at the ztryp1 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid Marian, *Chest* 108:255–65, 1995).

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region or corresponding human chromosomal region; and 3) cross-referencing model organisms, such as between mouse and human, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md.), and can be searched with a gene sequence of interest for the mapping data contained within these short genomic landmark STS sequences.

The present invention also provides reagents that will find use in diagnostic applications. For example, the ztryp1 gene, a probe comprising ztryp1 DNA or RNA or a subsequence thereof can be used to determine if the ztryp1 gene is present on human chromosome 11 or if a mutation has occurred. Based on syntenic data from the mouse ztryp1 (Example 3), human Ztryp1 is located at the 11q23-24 region of human chromosome 11. Detectable chromosomal aberrations at the ztryp1 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, fluorescence in situ hybridization methods, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The ztryp1 gene is located at the 11q23-24 region of chromosome 11. Several genes of known function or correlated with human disease map to this region. For example, many gross chromosomal abnormalities such as chromosomal deletions, or loss of heterogeneity (LOH), and translocations in the 11q23 region are associated with various human tumors, including lymphoid cancers such as acute lymphoid and myeloid leukemias (acute lymphoblastic leukemia (ALL); acute myeloid leukemia (AML); mixed lineage leukemias; MLL), breast and lung cancers, carotid body tumors and tumor suppressor gene on 11q is suspected to be involved (E.g., see Rowley, J D et al., *Proc. Nat'l. Acad. Sci.* 87:9358–9362, 1990; Zieman-van der Poel, S et al., *Proc. Nat'l. Acad. Sci.* 88:10735–10739, 1991; Iziuka, M et al., *Genes Chom. Cancer* 13:40–46, 1995; Murakami, Y et al., *Proc. Nat'l. Acad. Sci.* 95:8153–8158, 1998). Thus, ztryp1 polynucleotide probes can be used to detect abnormalities or genotypes associated with cancers and other diseases associated with chromosomal translocations in 11q23-q24. Further, ztryp1 polynucleotide probes can be used to detect abnormalities or genotypes associated with some genetically linked forms of tuberous sclerosis and Ewing sarcoma, wherein variants of the disease are linked to chromosomal translocation breakpoints in the 11q region between 11q22-24, such as reciprocal translocations involving 11q23-24 and chromosomes 22. Moreover, translocations between chromosomes 4, 9, 10 and 19 with the 11q23 locus are involved in many MLL and some ALL. In addition, the most frequent translocation seen hereditary in breast cancer is between 11q23 and 22q11 (Iselius, L. et al., *Hum. Genet*. 64:343–355, 1983; Lindblom, A et al., *Am. J. Hum>Genet*. 54:871–876, 1994); and deletion of 11q23-q24 (wherein the ztryp1 gene is located) is the most frequent chromosomal aberration in B-cell lymphomas (B-CLL) found in ataxia-telangiectasia (11q23.3) (Louis-Bar syndrome). Moreover, amongst other genetic loci, those for hydrolethalus syndrome (11q23-q25), neural cell adhesion molecule (NCAM) (11q23.1), and guanine nucleotide exchange factor (GEF) (11q23.3) all manifest themselves in human disease states as well as map to this region of the human genome. See the Online Mendellian Inheritance of Man (OMIM) gene map, and references therein, for this region of chromosome 11 on a publicly available WWW server (National Center for Biotechnology Information, National Library of Medicine, Bethesda, Md.), All of these serve as possible candidate genes for an inheritable disease that shows linkage to the same chromosomal region as the ztryp1 gene.

Similarly, defects in the ztryp1 locus itself may result in a heritable human disease state. As a protease, it may be involved in regulatory processes, such as cleaving regulatory signaling or cell cycle molecules to their active polypeptides, and as such may act directly or indirectly as a tumor suppressor. As such, mutations, LOH or translocations within the ztryp1 locus could result in formation or exacerbation of cancers (formation, cell transformation, metastasis, aggressiveness of tumors). As it is located on chromosome 11q23-q24, a region important in cancer, LOH of zrtyp1 may be involved in progression of human cancers and metastasis. Thus, deletions, rearrangements, or other defects in the ztryp1 gene itself can increase susceptibility to cancers, or other immune or testicular dysfunction. Moreover, defects in the ztryp1 gene may fully or in part cause known human diseases for which all the genetic defects are not known, for example, those diseases associated with Jacobsen's Syndrome (11q23-25 translocations), and hydrolethalus syndrome (11q23-q25). Molecules of the present invention, such as the polypeptides, antagonists, agonists, polynucleotides and antibodies of the present invention would aid in the detection, diagnosis prevention, and treatment associated with a ztryp1 genetic defect.

A diagnostic can assist physicians in determining the type of disease and appropriate associated therapy, or assistance in genetic counseling. As such, the inventive anti-ztryp1 antibodies, polynucleotides, and polypeptides can be used for the detection of ztryp1 polypeptide, mRNA or anti-ztryp1 antibodies, thus serving as markers and be directly used for detecting or genetic diseases or cancers, as described herein, using methods known in the art and described herein. As translocations within 11q23-q24 are frequently involved human cancers, as discussed above, there is great utility in having ztryp1 polynucleotide that probes can be used to detect abnormalities or genotypes associated with chromosome 11q23–24 deletions, LOH, and translocations associated with human diseases, other translocations involved with malignant progression of tumors or other 11q23-24 mutations, which are expected to be involved in chromosome rearrangements in malignancy; or in other cancers. Similarly, ztryp1 polynucleotide probes can be used to detect abnormalities or genotypes associated with chromosome 11q23-24 trisomy and chromosome loss. (e.g. LOH) associated with human diseases or spontaneous abortion. Thus, ztryp1 polynucleotide probes can be used to detect abnormalities or genotypes associated with these defects.

As discussed above, defects in the ztryp1 gene itself may result in a heritable human disease state. Molecules of the present invention, such as the polypeptides, antagonists, agonists, polynucleotides and antibodies of the present invention would aid in the detection, diagnosis prevention, and treatment associated with a ztryp1 genetic defect. In addition, ztryp1 polynucleotide probes can be used to detect allelic differences between diseased or non-diseased individuals at the ztryp1 chromosomal locus. As such, the ztryp1 sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14–17 nt). PCR primers are at least 5 nt in length, preferably 15 or more, more preferably 20–30 nt. For gross analysis of genes, or chromosomal DNA, a ztryp1 polynucleotide probe may comprise an entire exon or more. Exons are readily determined by one of skill in the art by comparing ztryp1 sequences (SEQ ID NO:1 or SEQ ID NO:14) with the genomic DNA for ztryp1. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a ztryp1 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a ztryp1 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the ztryp1 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1 or SEQ ID NO:14, the complement of SEQ ID NO:1 or SEQ ID NO:14, or an RNA equivalent thereof. Such methods of showing genetic linkage analysis to human disease phenotypes are well known in the art. For reference to PCR based methods in diagnostics see see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Aberrations associated with the ztryp1 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)). Direct analysis of an ztryp1 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Mice engineered to express the ztryp1 gene, referred to as "transgenic mice," and mice that exhibit a complete absence of ztryp1 gene function, referred to as "knockout mice," may also be generated (Snouwaert et al., *Science* 257:1083, 1992; Lowell et al., *Nature* 366:740–42, 1993; Capecchi, M. R., Science 244: 1288–1292, 1989; Palmiter, R. D. et al. *Annu Rev Genet*. 20: 465–499, 1986). For example, transgenic mice that over-express ztryp1, either ubiquitously or under a tissue-specific or tissue-restricted promoter can be used to ask whether over-expression causes a phenotype. For example, over-expression of a wild-type ztryp1 polypeptide, polypeptide fragment or a mutant thereof may alter normal cellular processes, resulting in a phenotype that identifies a tissue in which ztryp1 expression is functionally relevant and may indicate a therapeutic target for the ztryp1, its agonists or antagonists. For example, a preferred transgenic mouse to engineer is one that over-expresses the ztryp1 active polypeptide (approximately amino acids 44 (Val) to 276 (Ile) of SEQ ID NO:2; approximately amino acids 43 (Val) to 275 (Arg) of SEQ ID NO:15). Moreover, such over-expression may result in a phenotype that shows similarity with human diseases. Similarly, knockout ztryp1 mice can be used to determine where ztryp1 is absolutely required in vivo. The phenotype of knockout mice is predictive of the in vivo effects of that a ztryp1 antagonist, such as those described herein, may have. The mouse ztryp1 cDNA can be used to generate knockout mice or used to isolate murine ztryp1 mRNA, and genomic DNA, which are subsequently used to generate knockout mice. These mice may be employed to study the ztryp1 gene and the protein encoded thereby in an in vivo system, and can be used as in vivo models for corresponding human diseases. Moreover, transgenic mice expression of ztryp1 antisense polynucleotides or ribozymes directed against ztryp1, described herein, can be used analogously to transgenic mice described above.

Polynucleotides and polypeptides of the present invention will additionally find use as educational tools as a laboratory practicum kits for courses related to genetics and molecular biology, protein chemistry and antibody production and analysis. Due to its unique polynucleotide and polypeptide sequence molecules of Ztryp1 can be used as standards or as "unknowns" for testing purposes. For example, Ztryp1 polynucleotides can be used as an aid, such as, for example, to teach a student how to prepare expression constructs for bacterial, viral, and/or mammalian expression, including fusion constructs, wherein Ztryp1 is the gene to be expressed; for determining the restriction endonuclease cleavage sites of the polynucleotides; determining mRNA and DNA localization of Ztryp1 polynucleotides in tissues (i.e., by Northern and Southern blotting as well as polymerase chain reaction); and for identifying related polynucleotides and polypeptides by nucleic acid hybridization.

Ztryp1 polypeptides can be used educationally as an aid to teach preparation of antibodies; identifying proteins by Western blotting; protein purification; determining the weight of expressed Ztryp1 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., receptor binding, signal transduction, proliferation, and differentiation) in vitro and in vivo. Ztryp1 polypeptides can also be used to teach analytical skills such as mass spectrometry, circular dichroism to determine conformation, especially of the four alpha helices, x-ray crystallography to determine the three-dimensional structure in atomic detail, nuclear magnetic resonance spectroscopy to reveal the structure of proteins in solution. For example, a kit containing the Ztryp1 can be given to the student to analyze. Since the amino acid sequence would be known by the professor, the protein can be given to the student as a test to determine the skills or develop the skills of the student, the teacher would then know whether or not the student has correctly analyzed the polypeptide. Since every polypeptide is unique, the educational utility of Ztryp1 would be unique unto itself.

The antibodies which bind specifically to Ztryp1 can be used as a teaching aid to instruct students how to prepare affinity chromatography columns to purify Ztryp1, cloning and sequencing the polynucleotide that encodes an antibody and thus as a practicum for teaching a student how to design humanized antibodies. The Ztryp1 gene, polypeptide or antibody would then be packaged by reagent companies and sold to universities so that the students gain skill in art of molecular biology. Because each gene and protein is unique, each gene and protein creates unique challenges and learning experiences for students in a lab practicum. Such educational kits containing the Ztryp1 gene, polypeptide or antibody are considered within the scope of the present invention.

The invention is further illustrated by the following non-limiting examples.

EXAMPLES

Example 1

Identification of Mouse Ztryp1

Using an OST Sequence to Obtain Full-length Mouse Ztryp1

Scanning of sequence databases resulted in identification of an Omnibank Sequence Tag (OST; OST 1193) sequence, (Lexicon). Oligonucleotides ZC18,364 (SEQ ID NO:4) and ZC18,365 (SEQ ID NO:5) were designed from this sequence and used in a PCR to screen an arrayed mouse testis cDNA/plasmid library. Thermocycler conditions were as follows: 1 cycle at 94° C. for 1.5 min.; 35 cycles at 94° C. for 10 sec., 62° C. for 20 sec., 72° C. for 30 sec.; 1 cycle at 72° C. for 7 min.; followed by a 4° C. hold. The PCR product was run on a 2% Agarose gel to identify the 203 bp band expected for positive clones (those containing the OST). The library was de-convoluted down to a positive pool of 250 clones. *E.coli* DH10B cells (Gibco BRL) were transformed with this 250 clone pool by electroporation following manufacturer's protocol. The transformed culture was titered and then diluted and arrayed into 96 wells at approximately 20 cells/well. The cells were grown up in LB+amp overnight at 37° C. An aliquot of the cells were pelleted and a positive sub-pool was identified using a PCR screen, using the primers and conditions as described above. The remaining cells from the positive sub-pool were plated and colonies screened by PCR to identify a positive clone. Sequence analysis indicated that this clone was incomplete at the 5' end.

5' RACE was carried out with oligonucleotides ZC9,739 (SEQ ID NO:6) (AP1) and ZC18,364 (SEQ ID NO:4) using cDNA prepared from mouse testis RNA (Clontech) using a Marathon cDNA kit (Clontech). PCR conditions were as follows: one cycle at 94° C. for 2 minutes; 5 cycles at 94° C. for 30 seconds, 72° C. for 1.5 minutes; 30 cycles at 94° C. for 30 seconds, 64° C. for 20 seconds, 72° C. for 1 min. 15 sec.; one cycle at 72° C. for 5 minutes; followed by 4° C. hold. Using 5 $\mu l$ of a 5:100 dilution of the initial RACE reaction, nested RACE was carried out with oligonucleotides ZC9,719 (SEQ ID NO:7) (AP2) and ZC20,900 (SEQ ID NO:8). PCR conditions were as follows: one cycle at 94° C. for 3 minutes; 22 cycles at 94° C. for 30 sec., 62° C. for 20 sec., 72° C. for 40 sec.; one cycle at 72° C. for 5 min.; followed by 4° C. hold. The nested PCR reaction was electrophoresed on a 2% agarose gel and a 0.5 kb band was excised and gel purified using QiaexH reagents (Qiagen) according to the manufacturer's protocol. Sequence analysis of the isolated RACE product extended the 5' end of ztryp1 to the initiating MET. The full length sequence of mouse ztryp1 is shown in SEQ ID NO:1 and its corresponding amino acid sequence shown in SEQ ID NO:2.

Sequencing primers include: ZC14,063 (SEQ ID NO:9), ZC5,020 (SEQ ID NO:10), ZC18,364 (SEQ ID NO:4), ZC18,365 (SEQ ID NO:5), ZC20,771 (SEQ ID NO:11), ZC20,900 (SEQ ID NO:8) and ZC9,719 (SEQ ID NO:7).

Example 2

Tissue Expression of Mouse Ztryp1 Using Northern Analysis

Northern Analysis was performed using a Mouse Multiple Tissue Blot and Master Dot Blot from Clontech (Palo Alto, Calif.) to determine the tissue distribution of mouse ztryp1. A 203bp cDNA probe corresponding to ztryp1 (OST1193) was obtained using the PCR. Oligonucleotides ZC18,364 (SEQ ID NO:4) and ZC18,365 (SEQ ID NO:5) were used as primers. Marathon cDNA (Clontech) synthesized from mouse testis RNA was used as a template. The probe was purified using a Gel Extraction Kit (Qiagen, Chatsworth, Calif.) according to manufacturer's instructions. The probe was radioactively labeled using the Rediprime II DNA labeling kit (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution for the Northern blots. Hybridization took place overnight at 55° C. using $1.5\times10^6$ cpm/ml labeled probe. The blots were then washed in 2×SSC, 0.1% SDS at room temperature, then with 2×SSC, 0.1I% SDS at 65° C., followed by a wash in 0.1×SSC, 0.1% SDS at 65° C. The blots were exposed to Biomax film (Kodak, Rochester, N.Y.) for three days. A single transcript of approximately 1.5 kb was only seen in testis on the MTN blot. The Master Dot Blot also indicated testis-specific localization.

Example 3

Chromosomal Assignment and Placement of Murine Ztryp1

Murine Ztryp1 was mapped in mouse to chromosome 9 using the commercially available mouse T31 whole genome radiation hybrid (WGRH) panel (Research Genetics, Inc., Huntsville, AL) and Map Manager QT linkage analysis program. At P=0.0001, murine Ztryp1 linked to the marker D9Mit328 with a LOD score of 4.0. D9Mit328 has been mapped at 23 cM on mouse chromosome 9.

The T31 WGRH panel contains DNAs from each of 100 radiation hybrid clones, plus two control DNAs (the 129aa donor and the A23 recipient). For the mapping of murine Ztryp1 with the T31 WGRH panel, 20 $\mu l$ reactions were set up in 96-well microtiter plates (Stratagene, La Jolla, Calif.) and used in a "RoboCycler Gradient 96" thermal cycler (Stratagene). Each of the 102 PCR reactions consisted of 2 $\mu l$ 10×KlenTaq PCR reaction buffer (CLONTECH Laboratories, Inc., Palo Alto, Calif.), 1.6 $\mu l$ dNTPs mix (2.5 mM each, PERKIN-ELMER, Foster City, Calif.), 1 $\mu l$ sense primer, ZC22,855, (SEQ ID NO:12), 1 $\mu l$ antisense primer, ZC22,856 (SEQ ID NO:13), 2 $\mu l$ "RediLoad" (Research Genetics, Inc., Huntsville, Ala.), 0.4 $\mu l$ 50× Advantage KlenTaq Polymerase Mix (Clontech Laboratories, Inc.), 25 ng of DNA from an individual hybrid clone or control and $ddH_2O$ for a total volume of 20 $\mu l$. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 64° C. and 1 minute and 15 seconds extension at 72° C. followed by a final 1 cycle extension of 7 minutes at 72° C. The reactions were separated by electrophoresis on a 2% agarose gel (Life Technologies, Gaithersburg, Md.).

One of skill in the art would recognize that the syntenic region of the human chromosome that corresponds to the mouse chromosomal locus above is human chromosome 11q23-24.

Example 4

Identification and Cloning of Human Ztryp1 Using the Murine Ztryp1 Sequence Scanning of translated human DNA databases using the mouse ztryp1 sequence (SEQ ID NO:1) (Example 1)

resulted in identification of an expressed sequence tag (EST) sequence EST3528608 (Genbank Accession No. AW183721). Sequence analysis on a clone containing this EST was performed, confirming that the cDNA was a human ortholog of the ztryp1 mouse sequence (SEQ ID NO:1 and SEQ ID NO:2). The full-length human cDNA sequence was called human ztryp1. The human ztryp1 polynucleotide sequence is shown in SEQ ID NO:14, and the corresponding polypeptide sequence shown in SEQ ID NO:15.

Example 5

Tissue Distribution of Human Ztryp1 in Tissue Panels Using PCR

A panel of cDNAs from human tissues was screened for human ztryp1 expression using PCR. The panel was made in-house and contained 94 marathon cDNA and cDNA samples from various normal and cancerous human tissues and cell lines and is shown in Table 5, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21,195 (SEQ ID NO:17) and ZC21,196 (SEQ ID NO:18) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:19) and 3' alpha tubulin specific oligo primer ZC17,574 (SEQ ID NO:20) or 3' G3PDH specific oligo primer ZC17,600 (SEQ ID NO:21) and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2–100 pg/$\mu$l of cDNA. The PCR reactions for human ztryp1 were set up using oligos ZC28,936 (SEQ ID NO:22) and ZC28,937 (SEQ ID NO:23). The amplification was carried out as follows: 1 cycle at 94° C. for 2 minutes, 5 cycles of 94° C. for 15 seconds, 70° C. for 30 seconds, followed by 35 cycles at 94° C. for 15 seconds, 62° C. for 20 seconds and 72° C. for 30 seconds, followed by 1 cycle at 72° C. for 5 minutes. About 10 $\mu$l of the PCR reaction product was subjected to standard Agarose gel electrophoresis using a 4% agarose gel. The correct predicted DNA fragment size was observed in testis and kidney marathon cDNA and in-house testis libraries. As with the mouse ztryp1, the human ztryp1 appears for the most part to be testis-specific in its expression.

The DNA fragment from the testis library were excised and purified using a Gel Extraction Kit (Qiagen, Chatsworth, Calif.) according to manufacturer's instructions. Fragments were confirmed by sequencing to show that they were indeed human ztryp1.

TABLE 5

| Tissue/Cell line | # samples | Tissue/Cell line | # samples |
|---|---|---|---|
| Adrenal gland | 1 | Bone marrow | 2 |
| Bladder | 1 | Fetal brain | 2 |
| Bone Marrow | 1 | Islet | 1 |
| Brain | 1 | Prostate | 2 |
| Cervix | 1 | RPMI #1788 (ATCC # CCL-156) | 2 |
| Colon | 1 | Testis | 3 |
| Fetal brain | 1 | Thyroid | 1 |
| Fetal heart | 1 | adipocyte | 1 |
| Fetal kidney | 1 | brain | 1 |
| Fetal liver | 1 | HaCat-human keratinocytes | 1 |
| Fetal lung | 1 | HPV (ATCC # CRL-2221) | 1 |
| Fetal muscle | 1 | Fetal liver | 1 |
| Fetal skin | 1 | Prostate SM | 1 |
| Heart | 2 | CD3 + selected PBMC's Ionomycin + PMA stimulated | 1 |
| K562 (ATCC # CCL-243) | 1 | HPVS (ATCC # CRL-2221)-selected | 1 |
| Kidney | 1 | Heart | 1 |
| Liver | 1 | Pituitary | 1 |
| Lung | 1 | Placenta | 2 |
| Lymph node | 1 | Salivary gland | 1 |
| Melanoma | 1 | kidney | 1 |
| Pancreas | 1 | Spinal cord | 1 |
| Pituitary | 1 | Stomach tumor | 1 |
| Placenta | 1 | MG63 | 1 |
| Prostate | 1 | | |
| Rectum | 1 | | |
| Salivary Gland | 1 | | |
| Skeletal muscle | 1 | | |
| Small intestine | 1 | | |
| Spinal cord | 1 | | |
| Spleen | 1 | | |
| Stomach | 1 | | |
| Testis | 2 | | |
| Thymus | 1 | | |
| Thyroid | 1 | | |
| Trachea | 1 | | |
| Uterus | 1 | | |

TABLE 5-continued

| Tissue/Cell line | # samples | Tissue/Cell line | # samples |
|---|---|---|---|
| Esophagus tumor | 1 | | |
| Mammary gland | 1 | | |
| ovary | 1 | | |
| Liver tumor | 1 | | |
| Lung tumor | 1 | | |
| Ovarian tumor | 1 | | |
| Rectal tumor | 1 | | |
| Uterus tumor | 2 | | |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A fusion protein produced by a method comprising:

culturing a host cell into which has been introduced a vector comprising the following operably linked elements:

(a) a transcriptional promoter;

(b) a DNA construct encoding a fusion protein, wherein the DNA construct encodes a polypeptide that is selected from the group consisting of:

(i) the amino acid sequence of SEQ ID NO: 2 from residue number 1 (Met), to residue number 23 (Ser);

(ii) the amino acid sequence of SEQ ID NO: 15 from residue number 1 (Met), to residue number 18 (Ala);

(iii) the amino acid sequence of SEQ ID NO: 2 from residue number 24 (Leu), to residue number 43 (Lys);

(iv) the amino acid sequence of SEQ ID NO: 15 from residue number 19 (Arg), to residue number 42 (Arg);

(v) the amino acid sequence of SEQ ID NO: 2 from residue number 24 (Leu), to residue number 276 (Ile);

(vi) the amino acid sequence of SEQ ID NO: 15 from residue number 19 (Arg), to residue number 275 (Arg);

(vii) the amino acid sequence of SEQ ID NO: 2 from residue number 24 (Leu), to residue number 314 (Leu);

(viii) the amino acid sequence of SEQ ID NO:15 from residue number 19 (Arg), to residue number 312 (Leu);

(ix) the amino acid sequence of SEQ ID NO: 2 from residue number 44 (Val), to residue number 276 (Ile);

(x) the amino acid sequence of SEQ ID NO: 15 from residue number 43 (Val), to residue number 275 (Arg);

(xi) the amino acid sequence of SEQ ID NO: 2 from residue number 44 (Val), to residue number 314 (Leu);

(xii) the amino acid sequence of SEQ ID NO: 15 from residue number 43 (Val), to residue number 312 (Leu);

(xiii) the amino acid sequence of SEQ ID NO: 2 from residue number 277 (Lys), to residue number 314 (Leu);

(xiv) the amino acid sequence of SEQ ID NO:15 from residue number 276 (Thr), to residue number 312 (Leu); and (xv) the amino acid sequence of SEQ ID NO:24; and at least one other DNA segment encoding an additional polypeptide, wherein the first and other DNA segments are connected in-frame; and encode the fusion protein; and (c) a transcriptional terminator; and recovering the protein encoded by the DNA segment.

2. An isolated polypeptide comprising a sequence of amino acid residues selected from the group consisting of:

(a) the amino acid sequence as shown in SEQ ID NO:2 from amino acid number 44 (Val) to amino acid number 276 (Ile);

(b) the amino acid sequence as shown in SEQ ID NO:15 from amino acid number 43 (Val) to amino acid number 275 (Arg);

(c) the amino acid sequence as shown in SEQ ID NO:2 from amino acid number 24 (Leu) to amino acid number 276 (Ile);

(d) the amino acid sequence as shown in SEQ ID NO:15 from amino acid number 19 (Arg) to amino acid number 275 (Arg);

(e) the amino acid sequence as shown in SEQ ID NO:2 from amino acid number 44 (Val) to amino acid number 314 (Leu);

(f) the amino acid sequence as shown in SEQ ID NO:15 from amino acid number 43 (Val) to amino acid number 312 (Leu);

(g) the amino acid sequence as shown in SEQ ID NO: 2 from amino acid number 24 (Leu) to amino acid number 314 (Leu);

(h) the amino acid sequence as shown in SEQ ID NO: 15 from amino acid number 19 (Arg) to amino acid number 312 (Leu);

(i) the amino acid sequence as shown in SEQ ID NO:2 from amino acid number 1 (Met) to amino acid number 314 (Leu), (j) the amino acid sequence as shown in SEQ ID NO:15 from amino acid number 1 (Met) to amino acid number 312 (Leu), and (k) the amino acid sequence as shown in SEQ ID NO:24.

3. An isolated polypeptide according to claim 2, wherein the sequence of amino acid residues is as shown in SEQ ID NO:2 from amino acid number 44 (Val) to amino acid number 276 (Ile), or the sequence of amino acids is as shown in SEQ ID NO:15 from amino acid number 43 (Val) to amino acid number 275 (Arg).

4. An isolated polypeptide according to claim 2, consisting of a sequence of amino acid residues selected from the group consisting of:

(a) the amino acid sequence as shown in SEQ, ID NO:2 from amino acid number 44 (Val) to amino acid number 276 (Ile);

(b) the amino acid sequence as shown in SEQ ID NO:15 from amino acid number 43 (Val) to amino acid number 275 (Arg);

(c) the amino acid sequence as shown in SEQ ID NO:2 from amino acid number 24 (Leu) to amino acid number 276 (Ile);

(d) the amino acid sequence as shown in SEQ ID NO:15 from amino acid number 19 (Arg) to amino acid number 275 (Arg);

(e) the amino acid sequence as shown in SEQ ID NO:2 from amino acid number 44 (Val) to amino acid number 314 (Leu);

(f) the amino acid sequence as shown in SEQ ID NO:15 from amino acid number 43 (Val) to amino acid number 312 (Leu);

(g) the amino acid sequence as shown in SEQ ID NO: 2 from amino acid number 24 (Leu) to amino acid number 314 (Leu);

(h) the amino acid sequence as shown in SEQ ID NO: 15 from amino acid number 19 (Arg) to amino acid number 312 (Leu);

(i) the amino acid sequence as shown in SEQ ID NO:2 from amino acid number 1 (Met) to amino acid number 314 (Leu), (j) the amino acid sequence as shown in SEQ ID NO:15 from amino acid number 1 (Met) to amino acid number 312 (Leu), and (k) the amino acid sequence as shown in SEQ ID NO:24.

5. An isolated polypeptide according to claim 4, wherein the sequence of amino acid residues is as shown in SEQ ID NO:2 from amino acid number 44 (Val) to amino acid number 276 (Ile), or the sequence of amino acids is as shown in SEQ ID NO: 15 from amino acid number 43 (Val) to amino acid number 275 (Arg).

* * * * *